`US010550395B2`

United States Patent
Xiao et al.

(10) Patent No.: US 10,550,395 B2
(45) Date of Patent: Feb. 4, 2020

(54) MATERIALS AND METHODS FOR RAPID AND SENSITIVE DETECTION OF SMALL-MOLECULE TARGETS

(71) Applicants: Yi Xiao, Miami, FL (US); Haixiang Yu, Miami, FL (US)

(72) Inventors: Yi Xiao, Miami, FL (US); Haixiang Yu, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/947,315

(22) Filed: Apr. 6, 2018

(65) Prior Publication Data

US 2019/0309296 A1 Oct. 10, 2019

(51) Int. Cl.
*C12N 15/115* (2010.01)
*G01N 33/94* (2006.01)
*G01N 33/92* (2006.01)

(52) U.S. Cl.
CPC .......... *C12N 15/115* (2013.01); *G01N 33/92* (2013.01); *G01N 33/946* (2013.01); *C12N 2310/16* (2013.01)

(58) Field of Classification Search
CPC combination set(s) only.
See application file for complete search history.

(56) References Cited

U.S. PATENT DOCUMENTS

| 9,804,178 | B2 * | 10/2017 | Roncancio | G01N 33/946 |
|---|---|---|---|---|
| 2016/0131668 | A1 * | 5/2016 | Roncancio | G01N 33/946 |
| | | | | 436/501 |

OTHER PUBLICATIONS

He, et al. (2010) Fluorescence Aptameric Sensor for Strand Displacement Amplification Detection of Cocaine. Anal. Chem., v.82(4): 1358-64 (Year: 2010).*
Yu, et al. (2018, Anal. Chem., v.90, No. 3, pp. 1748-1758). (Year: 2018).*
Li, et al. (2015, Analyst, v.140:7918). (Year: 2015).*
Kent, et al. (2013) Anal. Chem., v.85:9916) (Year: 2013).*
Liu, J., Lu, Y., "Fast Colorimetric Sensing of Adenosine and Cocaine Based on a General Sensor Design Involving Aptamers and Nanoparticles." Angew. Chem. Int. Ed, 2006, 45: 90-94.
Roncancio, D. et al., "A Label-Free Aptamer-Fluorophore Assembly for Rapid and Specific Detection of Cocaine in Biofluids." Analytical Chemistry, 2014, 86: 11100-11106.
Stojanovic, M. N., Landry, D. W., "Aptamer-Based Colorimetric Probe for Cocaine." J. Am. Chem. Soc., 2002, 124: 9678-9679.
Xia, F. et al., "Colorimetric detection of DNA, small molecules, proteins, and ions using unmodified gold nanoparticles and conjugated polyelectrolytes." PNAS, Jun. 2010, 107 (24): 10837-10841.
Zhang, J. et al., "Visual Cocaine Detection with Gold Nanoparticles and Rationally Engineered Aptamer Structures." Small, 2008, 4 (8): 1196-1200.
Zhu, Z. et al., "An Aptamer Cross-Linked Hydrogel as a Colorimetric Platform for Visual Detection." Angew. Chem. Int. Ed., 2010, 49: 1052-1056.

* cited by examiner

*Primary Examiner* — Jennifer Pitrak McDonald
(74) *Attorney, Agent, or Firm* — Saliwanchik, Lloyd & Eisenschenk

(57) ABSTRACT

The subject invention provides methods, assays and products for detecting small-molecules in a sample, in particular, in both clinical and field settings. The method for detecting a small-molecule target in a sample comprises providing a sample, contacting the sample with an aptamer-based sensor selective for the small-molecule target, and sensitively and rapidly detecting the small-molecule target in the sample. Specifically, the method utilizes EATR-amplified small-molecule sensors based on cooperative binding split aptamers (CBSAs).

8 Claims, 20 Drawing Sheets

Specification includes a Sequence Listing.

FIG. 3A 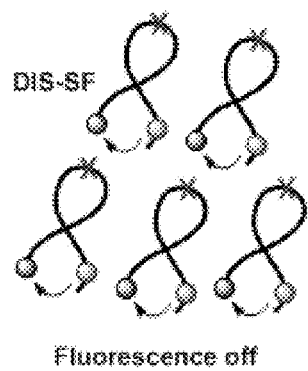 FIG. 3B FIG. 3C 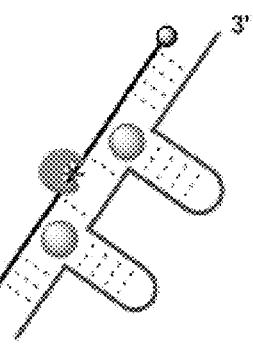
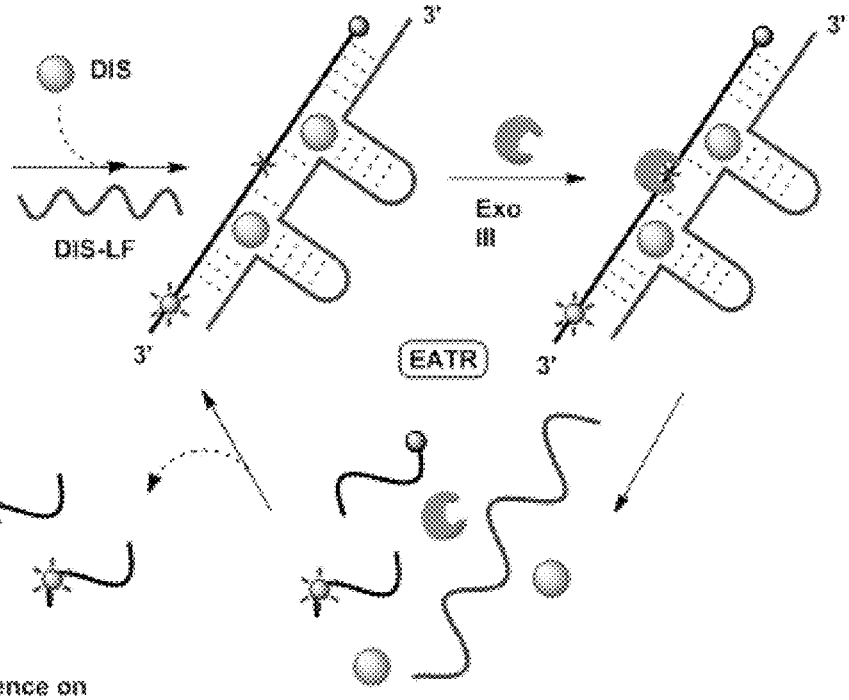
FIG. 3E  FIG. 3D
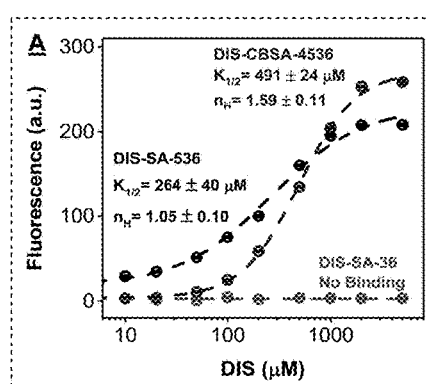 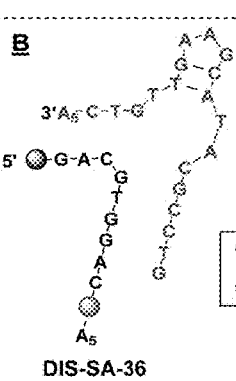 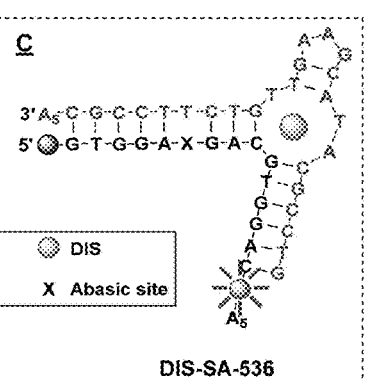
FIG. 4A  FIG. 4B  FIG. 4C

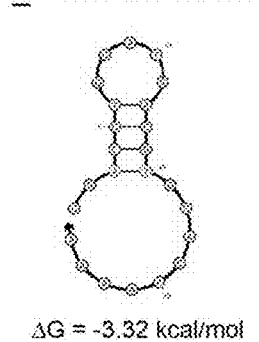
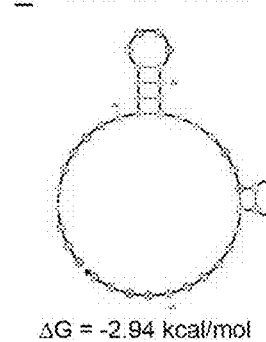
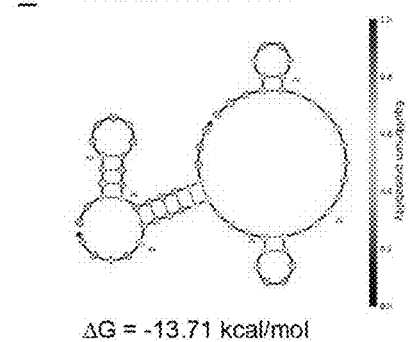
FIG. 5A    FIG. 5B    FIG. 5C
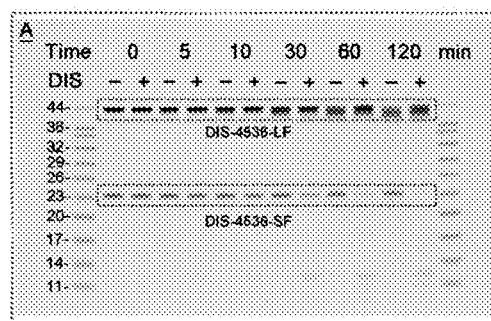
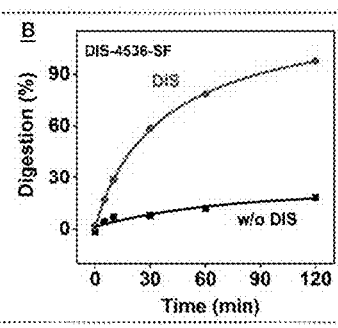
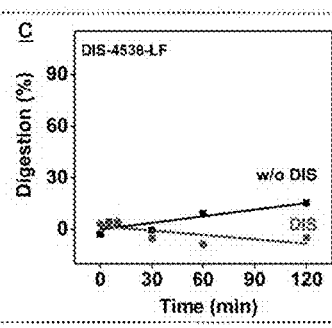
FIG. 6A    FIG. 6B    FIG. 6C
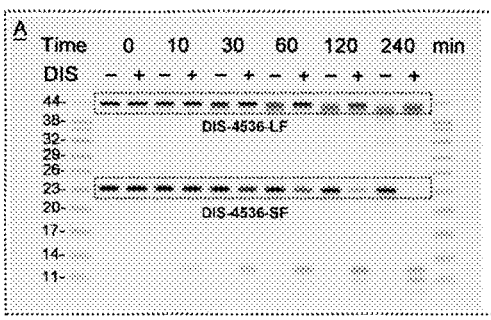
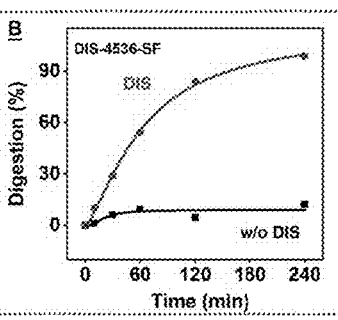
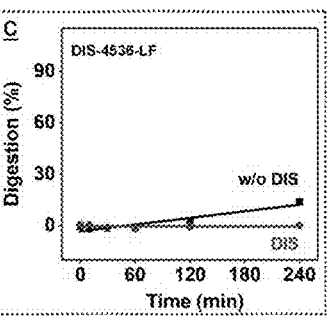
FIG. 7A    FIG. 7B    FIG. 7C

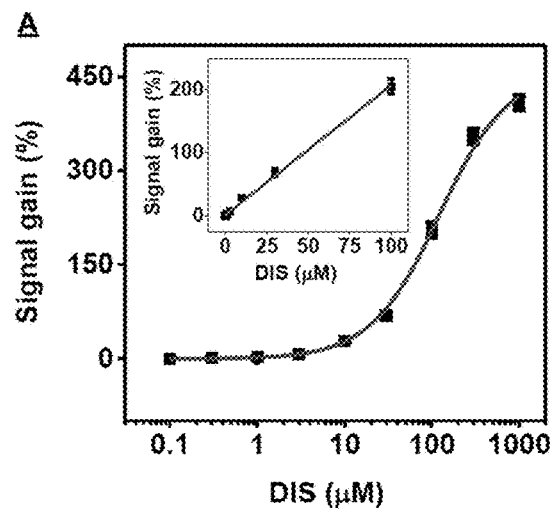
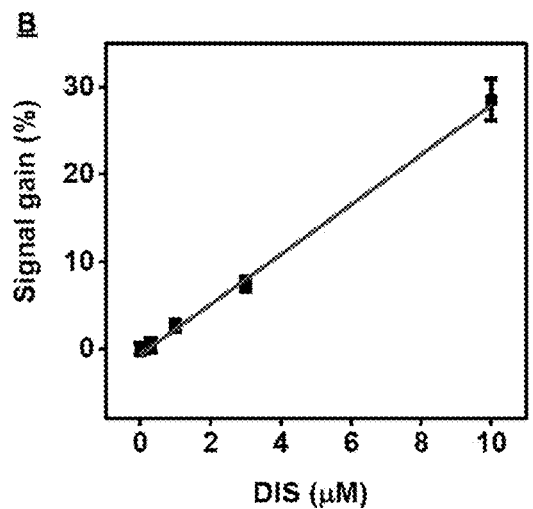
FIG. 10A
FIG. 10B
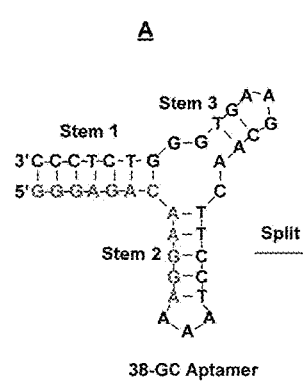
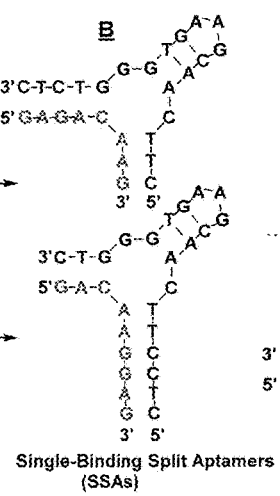
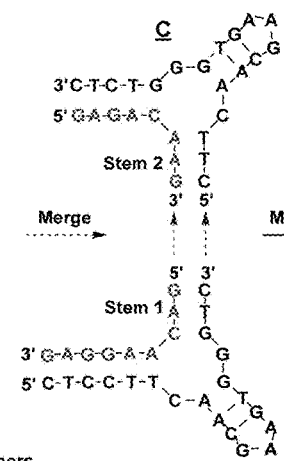
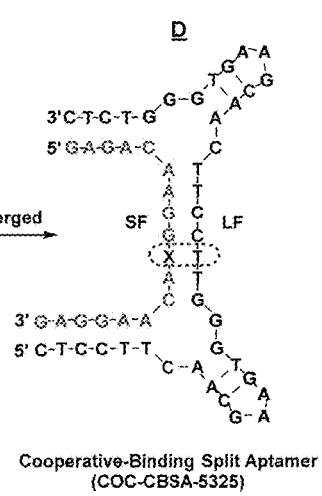
FIG. 11A
FIG. 11B
FIG. 11C
FIG. 11D

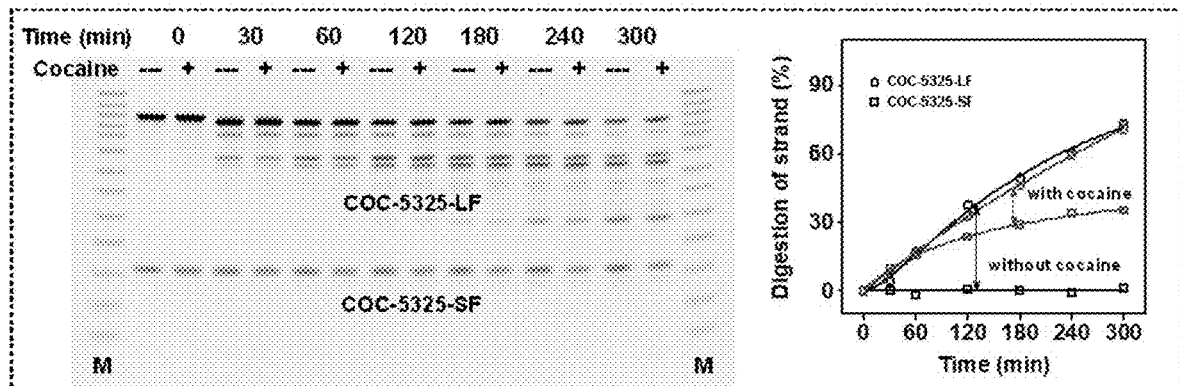
FIG. 15
FIG. 16A
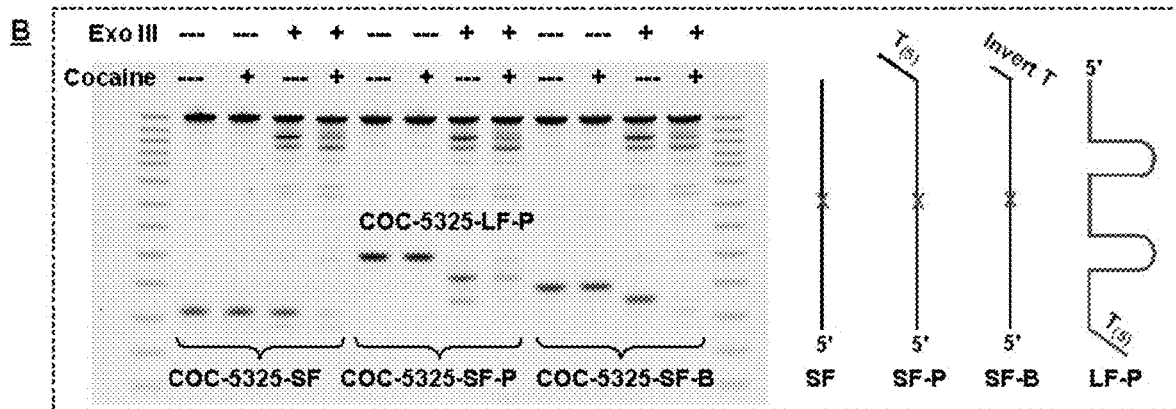
FIG. 16B

FIG. 25A  FIG. 25B  FIG. 25C
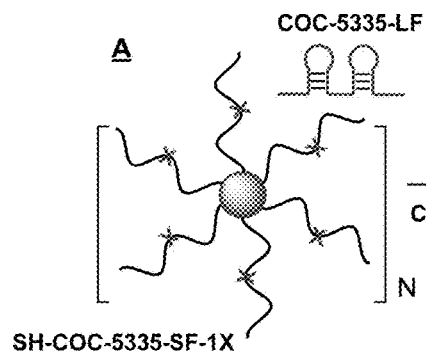 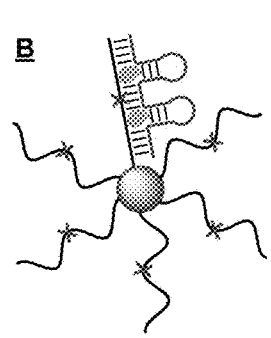 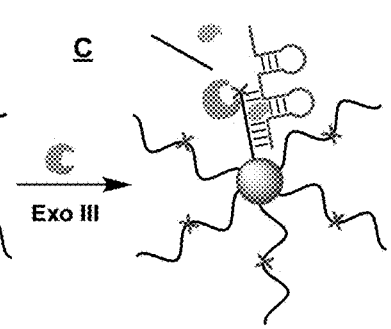
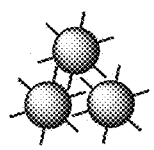 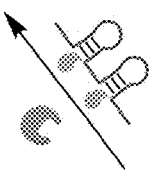 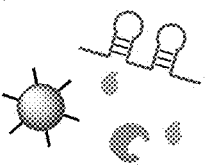 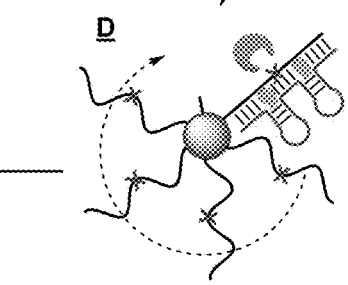
FIG. 25F  FIG. 25E  FIG. 25D
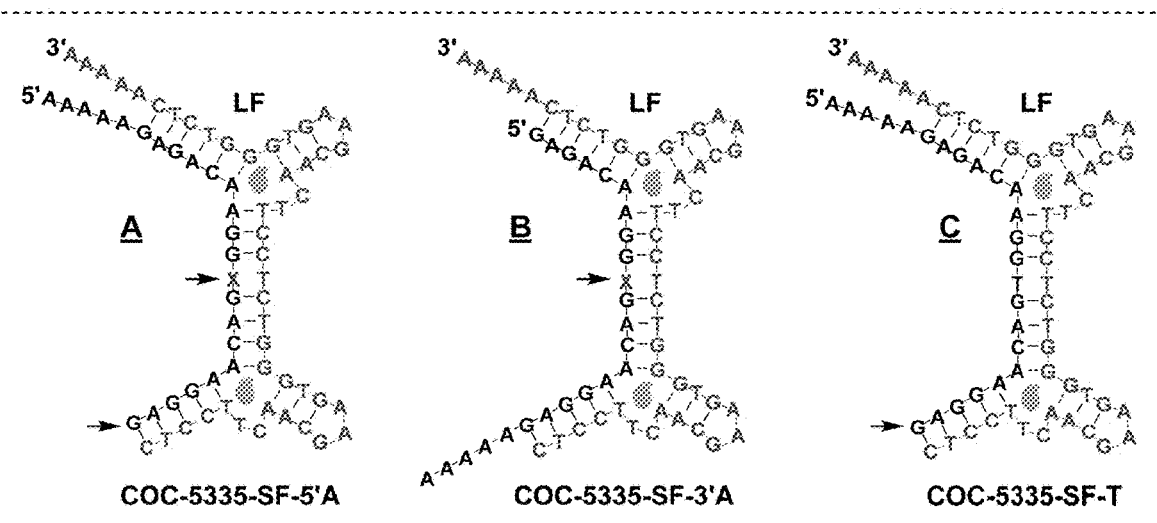
FIG. 26A  FIG. 26B  FIG. 26C

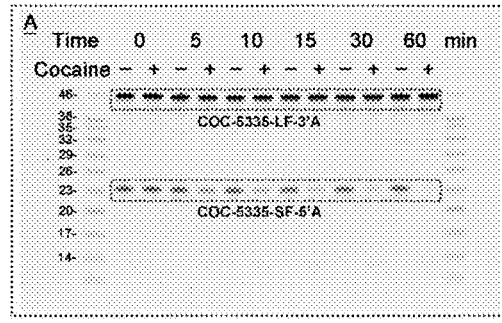 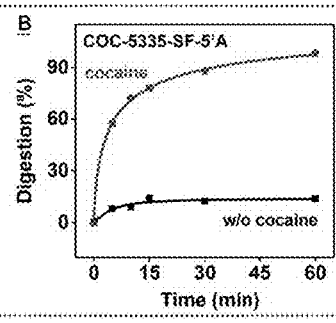 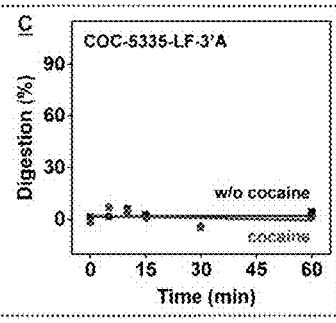
FIG. 27A　　　　　FIG. 27B　　　　　FIG. 27C
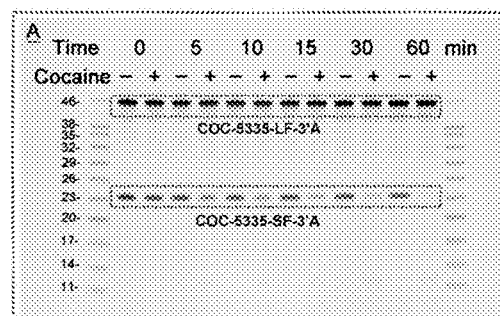 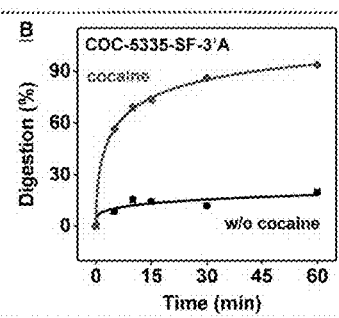 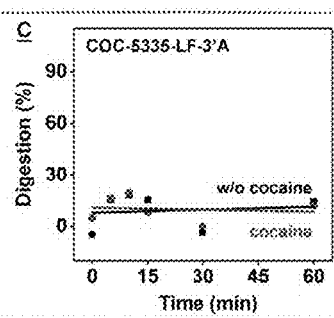
FIG. 28A　　　　　FIG. 28B　　　　　FIG. 28C
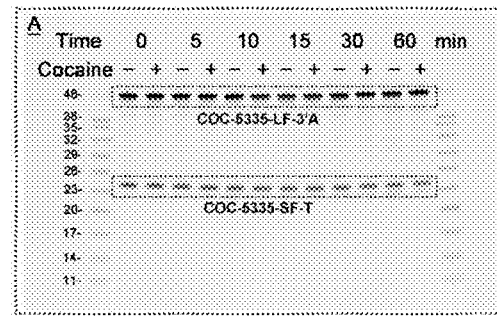 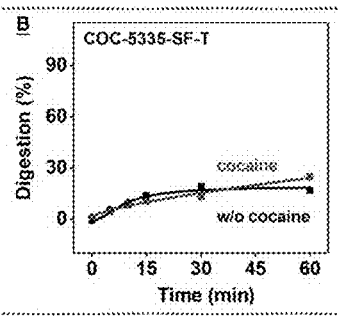 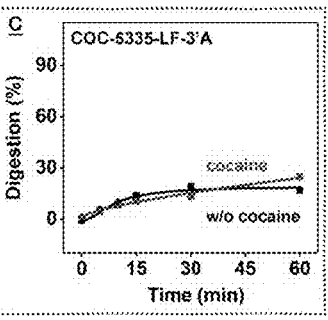
FIG. 29A　　　　　FIG. 29B　　　　　FIG. 29C FIG. 32A
FIG. 32B
FIG. 32C
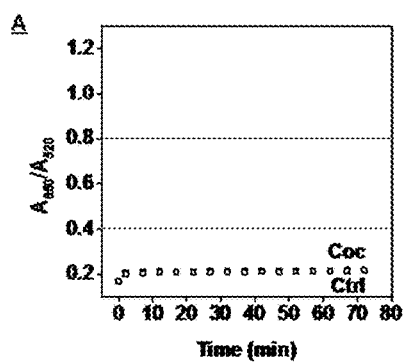
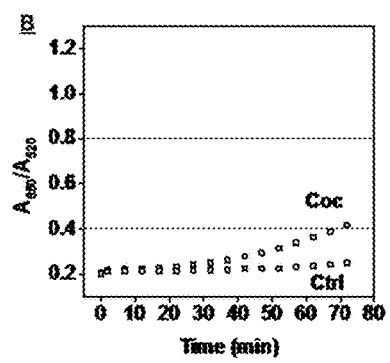
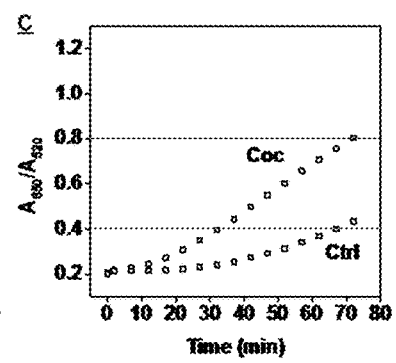
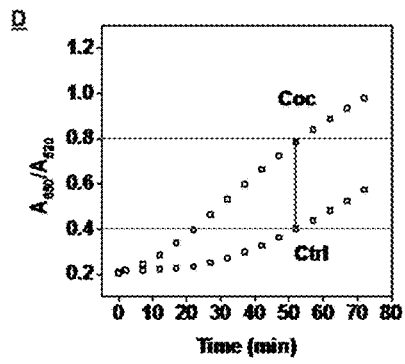
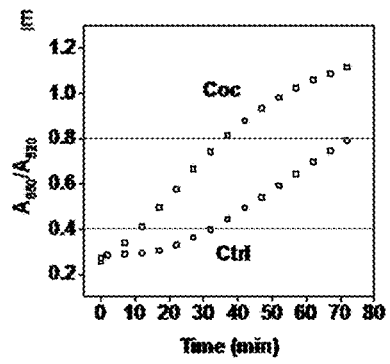
FIG. 32D
FIG. 32E
FIG. 32F FIG. 33A  FIG. 33B  FIG. 33C
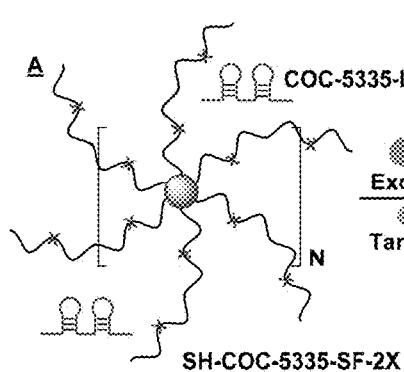
FIG. 33F  FIG. 33E  FIG. 33D
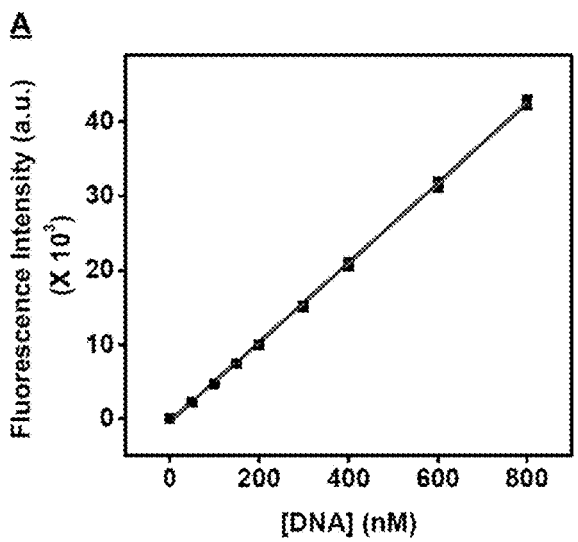
FIG. 34A
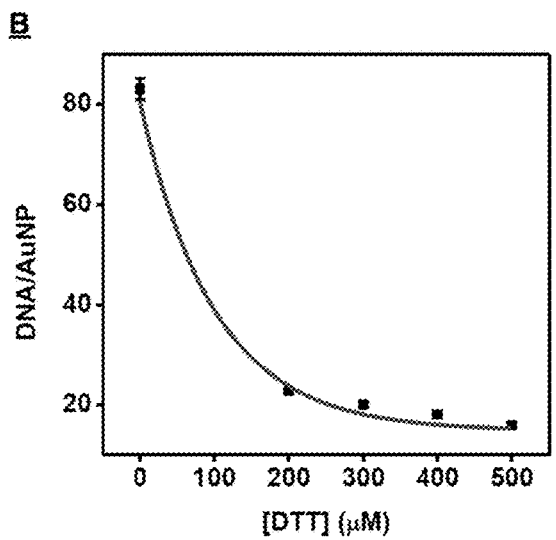
FIG. 34B FIG. 35A
FIG. 35B
FIG. 35C
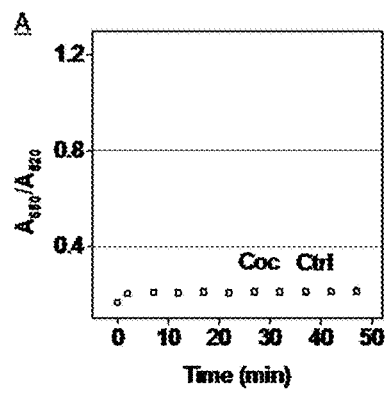
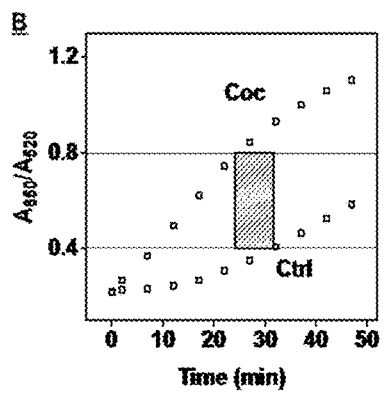
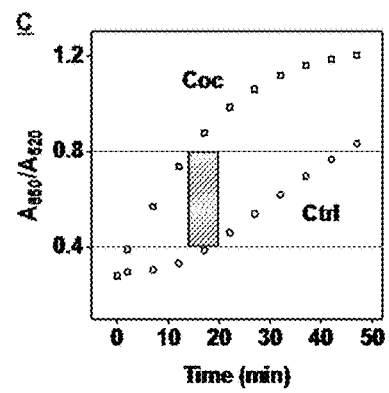
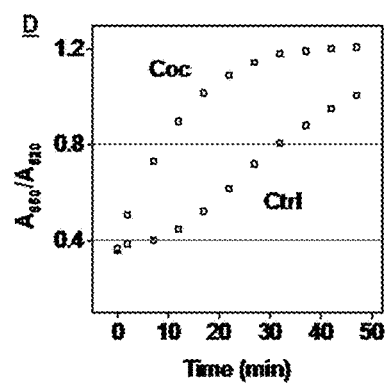
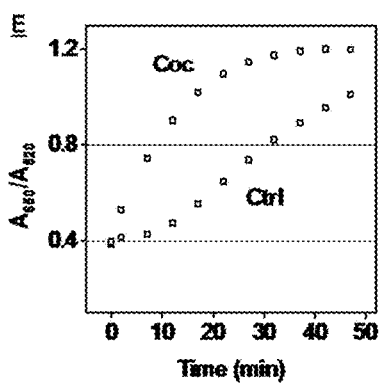
FIG. 35D
FIG. 35E
FIG. 35F
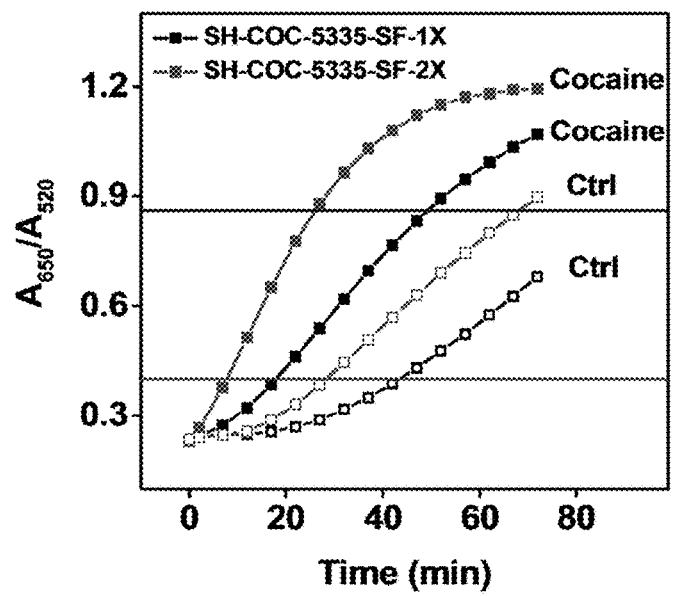
FIG. 36

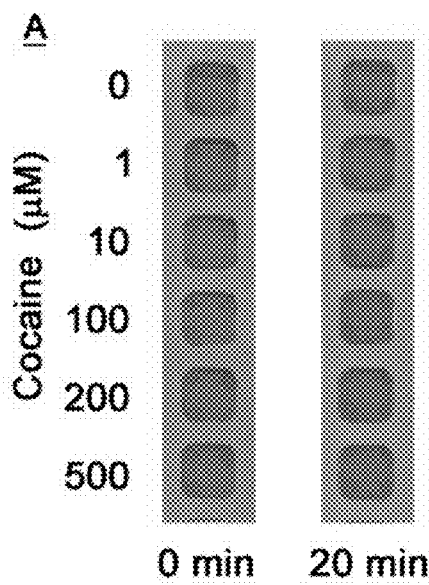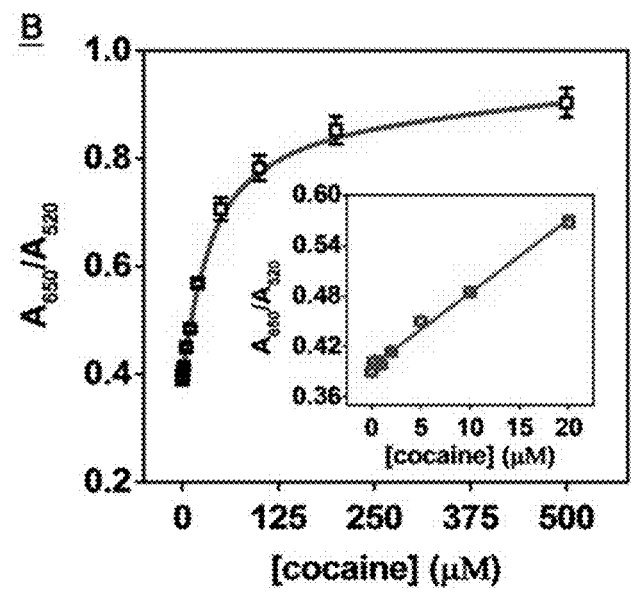
FIG. 37A  FIG. 37B
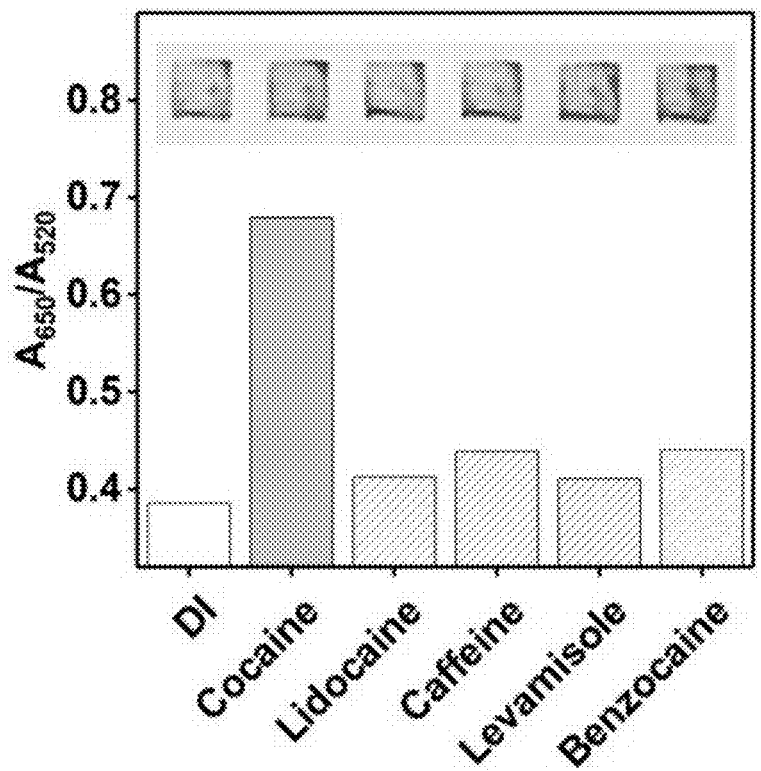
FIG. 38

SEQUENCE LISTING

```
<160> NUMBER OF SEQ ID NOS: 28

<210> SEQ ID NO 1
<211> LENGTH: 39
<212> TYPE: DNA
<213> ORGANISM: Artificial
<220> FEATURE:
<223> OTHER INFORMATION: aptamer

<400> SEQUENCE: 1
ctcgggacgt ggattttccg catacgaagt tgtcccgag                              39

<210> SEQ ID NO 2
<211> LENGTH: 44
<212> TYPE: DNA
<213> ORGANISM: Artificial
<220> FEATURE:
<223> OTHER INFORMATION: aptamer

<400> SEQUENCE: 2
gtccgcatac gaagttgtct tccgcatacg aagttgtcca aaaa                        44

<210> SEQ ID NO 3
<211> LENGTH: 23
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(1)
<223> OTHER INFORMATION: Iowa Black RQ quencher modification
<220> FEATURE:
<221> NAME/KEY: misc_feature
<222> LOCATION: (9)..(9)
<223> OTHER INFORMATION: internal C3 spacer modification
<220> FEATURE:
<221> NAME/KEY: misc_feature
<222> LOCATION: (18)..(18)
<223> OTHER INFORMATION: Cy5 fluorophore modification

<400> SEQUENCE: 3
ggacgtggag acgtggacaa aaa                                              23

<210> SEQ ID NO 4
<211> LENGTH: 24
<212> TYPE: DNA
<213> ORGANISM: Artificial
<220> FEATURE:
<223> OTHER INFORMATION: aptamer
```

```
<400> SEQUENCE: 4
gtccgcatac gaagttgtca aaaa                                              24

<210> SEQ ID NO 5
<211> LENGTH: 14
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(1)
<223> OTHER INFORMATION: Iowa Black RQ quencher modification
<220> FEATURE:
<221> NAME/KEY: misc_feature
<222> LOCATION: (9)..(9)
<223> OTHER INFORMATION: Cy5 fluorophore modification

<400> SEQUENCE: 5
gacgtggaca aaaa                                                         14

<210> SEQ ID NO 6
<211> LENGTH: 30
<212> TYPE: DNA
<213> ORGANISM: Artificial
<220> FEATURE:
<223> OTHER INFORMATION: aptamer

<400> SEQUENCE: 6
gtccgcatac gaagttgtct tccgcaaaaa                                        30

<210> SEQ ID NO 7
<211> LENGTH: 19
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(1)
<223> OTHER INFORMATION: Iowa Black RQ quencher modification
<220> FEATURE:
<221> NAME/KEY: misc_feature
<222> LOCATION: (5)..(5)
<223> OTHER INFORMATION: internal C3 spacer modification
<220> FEATURE:
<221> NAME/KEY: misc_feature
<222> LOCATION: (14)..(14)
<223> OTHER INFORMATION: Cy5 fluorophore modification

<400> SEQUENCE: 7
gtggagacgt ggacaaaaa                                                    19

<210> SEQ ID NO 8
<211> LENGTH: 23
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (9)..(9)
<223> OTHER INFORMATION: internal C3 spacer modification

<400> SEQUENCE: 8
ggacgtggag acgtggacaa aaa                                               23

<210> SEQ ID NO 9
<211> LENGTH: 40
```

```
<212> TYPE: DNA
<213> ORGANISM: Artificial
<220> FEATURE:
<223> OTHER INFORMATION: aptamer

<400> SEQUENCE: 9
ctccttcaac gaagtgggtt ccttcaacga agtgggtctc                            40

<210> SEQ ID NO 10
<211> LENGTH: 17
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (9)..(9)
<223> OTHER INFORMATION: internal C3 spacer modification

<400> SEQUENCE: 10
gagacaagga caaggag                                                    17

<210> SEQ ID NO 11
<211> LENGTH: 41
<212> TYPE: DNA
<213> ORGANISM: Artificial
<220> FEATURE:
<223> OTHER INFORMATION: aptamer

<400> SEQUENCE: 11
ctccttcaac gaagtgggtc tccttcaacg aagtgggtct c                          41

<210> SEQ ID NO 12
<211> LENGTH: 18
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (9)..(9)
<223> OTHER INFORMATION: internal C3 spacer modification

<400> SEQUENCE: 12
gagacaaggg acaaggag                                                   18

<210> SEQ ID NO 13
<211> LENGTH: 42
<212> TYPE: DNA
<213> ORGANISM: Artificial
<220> FEATURE:
<223> OTHER INFORMATION: aptamer

<400> SEQUENCE: 13
ctccttcaac gaagtgggtc ttccttcaac gaagtgggtc tc                         42

<210> SEQ ID NO 14
<211> LENGTH: 19
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (10)..(10)
<223> OTHER INFORMATION: internal C3 spacer modification

<400> SEQUENCE: 14
```
gagacaagga gacaaggag                                                    19

<210> SEQ ID NO 15
<211> LENGTH: 43
<212> TYPE: DNA
<213> ORGANISM: Artificial
<220> FEATURE:
<223> OTHER INFORMATION: aptamer

<400> SEQUENCE: 15
ctccttcaac gaagtgggtt cttccttcaa cgaagtgggt ctc                         43

<210> SEQ ID NO 16
<211> LENGTH: 20
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (10)..(10)
<223> OTHER INFORMATION: internal C3 spacer modification

<400> SEQUENCE: 16
gagacaagga gaacaaggag                                                   20

<210> SEQ ID NO 17
<211> LENGTH: 45
<212> TYPE: DNA
<213> ORGANISM: Artificial
<220> FEATURE:
<223> OTHER INFORMATION: aptamer

<400> SEQUENCE: 17
ctccttcaac gaagtgggtt ccttcaacga agtgggtctc ttttt                       45

<210> SEQ ID NO 18
<211> LENGTH: 41
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (41)..(41)
<223> OTHER INFORMATION: a 3' inverted deoxythymidine

<400> SEQUENCE: 18
ctccttcaac gaagtgggtt ccttcaacga agtgggtctc t                           41

<210> SEQ ID NO 19
<211> LENGTH: 22
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (9)..(9)
<223> OTHER INFORMATION: internal C3 spacer modification

<400> SEQUENCE: 19
gagacaagga caaggagttt tt                                                22

<210> SEQ ID NO 20
<211> LENGTH: 18
<212> TYPE: DNA
<213> ORGANISM: Artificial

```
<220> FEATURE:
<223> OTHER INFORMATION: aptamer
<220> FEATURE:
<221> NAME/KEY: misc_feature
<222> LOCATION: (9)..(9)
<223> OTHER INFORMATION: internal C3 spacer modification
<220> FEATURE:
<221> NAME/KEY: misc_feature
<222> LOCATION: (18)..(18)
<223> OTHER INFORMATION: a 3' inverted deoxythymidine

<400> SEQUENCE: 20
gagacaagga caaggagt                                                    18

<210> SEQ ID NO 21
<211> LENGTH: 18
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(1)
<223> OTHER INFORMATION: Iowa Black RQ quencher modification
<220> FEATURE:
<221> NAME/KEY: misc_feature
<222> LOCATION: (9)..(9)
<223> OTHER INFORMATION: internal C3 spacer modification
<220> FEATURE:
<221> NAME/KEY: misc_feature
<222> LOCATION: (18)..(18)
<223> OTHER INFORMATION: Cy5 fluorophore modification and a 3' inverted
      deoxythymidine

<400> SEQUENCE: 21
gagacaagga caaggagt                                                    18

<210> SEQ ID NO 22
<211> LENGTH: 58
<212> TYPE: DNA
<213> ORGANISM: Artificial
<220> FEATURE:
<223> OTHER INFORMATION: aptamer

<400> SEQUENCE: 22
ctccttcaac gaagtgggtt ccttcaacga agtgggtctc tttttttttt tttttttt       58

<210> SEQ ID NO 23
<211> LENGTH: 24
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (15)..(15)
<223> OTHER INFORMATION: internal C3 spacer modification

<400> SEQUENCE: 23 tttttttgaga caagggacaa ggag                                            24

<210> SEQ ID NO 24
<211> LENGTH: 46
<212> TYPE: DNA
<213> ORGANISM: Artificial
<220> FEATURE:
<223> OTHER INFORMATION: aptamer

<400> SEQUENCE: 24
ctccttcaac gaagtgggtc tccttcaacg aagtgggtct caaaaa                     46
```

```
<210> SEQ ID NO 25
<211> LENGTH: 23
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (14)..(14)
<223> OTHER INFORMATION: internal C3 spacer modification

<400> SEQUENCE: 25
aaaaagagac aagggacaag gag                                              23

<210> SEQ ID NO 26
<211> LENGTH: 23
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (9)..(9)
<223> OTHER INFORMATION: internal C3 spacer modification

<400> SEQUENCE: 26
gagacaaggg acaaggagaa aaa                                              23

<210> SEQ ID NO 27
<211> LENGTH: 24
<212> TYPE: DNA
<213> ORGANISM: Artificial
<220> FEATURE:
<223> OTHER INFORMATION: aptamer

<400> SEQUENCE: 27
aaaaagagac aaggtgacaa ggag                                             24

<210> SEQ ID NO 28
<211> LENGTH: 48
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (15)..(15)
<223> OTHER INFORMATION: internal C3 spacer modification
<220> FEATURE:
<221> NAME/KEY: misc_feature
<222> LOCATION: (39)..(39)
<223> OTHER INFORMATION: internal C3 spacer modification

<400> SEQUENCE: 28 tttttgaga caagggacaa ggagttttt gagacaaggg acaaggag                    48
```

MATERIALS AND METHODS FOR RAPID AND SENSITIVE DETECTION OF SMALL-MOLECULE TARGETS

GOVERNMENT SUPPORT

This invention was made with government support under 2013-DN-BX-K032 and 2015-R2-CX-0034 awarded by The National Institute of Justice, and DA036821 awarded by National Institutes of Health. The government has certain rights in the invention.

SEQUENCE LISTING

The Sequence Listing for this application is labeled "SeqList-04Apr18-ST25.txt," which was created on Apr. 4, 2018, and is 8 KB. The Sequence Listing is incorporated herein by reference in its entirety.

BACKGROUND

The biosensor field is on a continuous quest for ever-greater sensitivity. In conventional bioassays, where the signal is directly proportional to the target concentration, the sensitivity is determined by the intrinsic target affinity of the bioreceptor being used for detection. In this scenario, it would be difficult to generate a measurable signal at target concentrations more than 100-fold lower than the dissociation constant ($K_D$) of the bioreceptor. Accordingly, many amplification approaches have been developed in which one binding event can generate multiple signals, allowing detection of targets at very low concentrations.

Enzyme-assisted target recycling (EATR) has proven to be an especially effective way to amplify signals generated from target-binding events. This approach relies on selective, nuclease-mediated degradation of the probe strand of a target-probe duplex that only forms in the presence of the target; this liberates the target, which is 'recycled' for use in additional digestion reactions. Thus, through EATR, a substantial fluorescent signal can be generated by a single copy of the target, thereby greatly decreasing the limit of detection.

Aptamers are nucleic acid-based bio-recognition elements that are isolated in vitro through processes based on systematic evolution of ligands by exponential enrichment (SELEX). Aptamers can bind to a wide variety of targets, including proteins, metal ions, small molecules, and even whole cells. Aptamer-based biosensors have been developed for environmental monitoring, drug detection, and medical diagnostics.

Aptamer-based sensors have many advantages compared to other state-of-the-art methods for the detection of small-molecule targets. Instrumental methods, such as gas or liquid chromatography/mass spectrometry, are sensitive and specific; however, these methods require laborious sample preparation and instruments that are cumbersome and sophisticated, limiting their use for on-site and high-throughput detection. Antibody-based immunoassays, such as ELISA, are highly sensitive and offer high target specificity; however, the in vivo processes for antibody generation are tedious, costly, and challenging, especially for non-immunogenic small molecules. On the other hand, aptamers can be isolated rapidly with controllable affinity and specificity, and are produced without batch-to-batch variation. Additionally, DNA aptamers can be used under harsh conditions and have long shelf lives due to their high chemical stability.

Many strategies have been employed in aptamer-based assays to achieve target detection in an instrument-free manner. In particular, aptamers can be split into two or three fragments that remain separate in the absence of target but assemble upon target binding, and such split-aptamer based sensors have gained popularity as a potential strategy for effective signal reporting.

In principle, the target-induced assembly of split aptamers should be compatible with EATR-mediated signal amplification. Ideally, the split fragments should be highly responsive to target-induced assembly and only the target-aptamer complex should be specifically recognized and digested by the enzyme. However, it is difficult to achieve sensitive target-induced aptamer assembly with conventional split aptamers with a single binding-domain. Small-molecule-binding split aptamers usually have equilibrium dissociation constants ($K_D$) in the high micromolar range, such that no measurable target-induced aptamer assembly can be observed even with a high concentration of targets. Although target affinity can be improved by engineering split aptamers with longer complementary stems, the majority of thermostable split aptamers undergo some degree of pre-assembly in the absence of target, thereby producing high background signal. Second, in contrast to DNA-based EATR assays, in which target-binding always converts a stem-loop probe structure into a probe-target duplex, aptamer-target binding often gives rise to complex tertiary structures that are non-ideal substrates for nucleases.

Therefore, there is a need for the development of aptamer-based sensors for use in EATR assays. There is also a need for accurate, rapid, sensitive, and powerful means for small-molecule detection by employing EATR assay with aptamer-based sensors.

BRIEF SUMMARY

The subject invention provides methods, assays, and products for detecting small molecules in a complex sample, in particular, in both clinical and field settings. In one embodiment, the method comprises contacting the sample with an aptamer-based sensor selective for a small-molecule target, and detecting the small-molecule target in the sample. Preferably, the aptamer-based sensor is a split aptamer selective for the small-molecule target in the sample.

In one embodiment, the sample is a biological sample of a subject. In a specific embodiment, the biological sample is selected from blood, plasma, urine, tears, and saliva. The subject may be any animal or human, preferably, human. The subjects may also refer to any animal including, but not limited to, non-human primates, rodents, rodents, dogs, cats, horses, cattle, pigs, sheep, goats, chickens, guinea pigs, hamsters and the like.

In one embodiment, the sample is an environmental sample, for example, a water, soil, air, or plant sample. In another embodiment, the sample is a seized drug sample, for instance, a street drug sample seized by law enforcement or government officials.

In one embodiment, the detection of the small-molecule target comprises measuring a signal generated upon assembly of the aptamer-target complex. In another embodiment, the method further comprises determining the concentration of the small-molecule target in the sample.

In one embodiment, the aptamer-based sensor is a cooperative binding split aptamer (CBSA). In one embodiment, the subject invention provides a method for engineering and generating cooperative binding split aptamers (CBSAs) selective for small-molecule targets. CBSAs can be engineered from parent split aptamers comprising a single target-binding domain and comprise a short fragment and a long fragment.

In one embodiment, CBSAs contain two target-binding domains. Advantageously, CBSAs with two target-binding domains exhibit enhanced target response compared with single-domain split aptamers. The first binding event partially stabilizes the CBSA structure and facilitates the second binding event. This cooperative assembly can reduce the target concentration required to assemble the CBSA several-fold, resulting in far greater specificity and sensitivity relative to the parent split aptamer.

In one embodiment, the subject invention provides a method for detecting a small-molecule target in a sample using CBSAs, comprising contacting the sample with a CBSA selective for the small-molecule target to form a CBSA-target complex, and detecting the small-molecule target in the sample by measuring a signal generated upon assembly of the CBSA-target complex.

In one embodiment, the method for detecting a small-molecule in a sample further comprises an EATR-amplified assay that employs CBSAs as EATR-amplified biosensors. Advantageously, the methods utilizing CBSA-based, EATR-amplified assays are rapid, sensitive, and specific for the detection of various small-molecule targets.

In another embodiment, the subjection invention provides an approach for the development of rapid and sensitive EATR-amplified small-molecule sensors based on CBSAs.

In a specific embodiment, a duplexed C3 spacer abasic site is introduced between the two binding domains in the short fragment, enabling EATR signal amplification through exonuclease III's (Exo III) apurinic endonuclease activity. When the CBSA assembles, the resulting duplex at the abasic site is recognized and cleaved by Exo III.

In one embodiment, the subject invention also provides an instrument-free colorimetric assay employing EATR-mediated aggregation of CBSA-modified gold nanoparticles (AuNPs) for the rapid detection of small molecules at very low micromolar concentration. This assay utilizes an EATR-amplified sensor conjugated to the surface of AuNPs.

In one embodiment, the subject invention provides a method for detecting cocaine in a sample using CBSA-based EATR-amplified fluorescence and colorimetric assays. The method comprises contacting the sample with CBSA selective to cocaine, and detecting cocaine in the sample. The method can further comprise introducing Exo III into the sample.

In one embodiment, the subject invention provides a method for detecting dehydroisoandrosterone-3-sulfate (DIS) in a sample using CBSA-based EATR-amplified fluorescence and colorimetric assays. The method comprises providing a sample, contacting the sample with a CBSA selective to DIS, and detecting DIS in the sample. The method further comprises introducing Exo III in the sample, resulting in recycling of the long fragment and DIS molecules for further rounds of binding, while releasing a fluorescent signal for each binding event.

In one embodiment, the subject invention also provides a method for detecting small molecules that are biomarkers for disease diagnosis, or monitoring a therapeutic response to specific drugs. In specific embodiments, the condition can be cancer, an inflammatory disease, or a neurodegenerative disease. The condition can also be an injury.

BRIEF DESCRIPTION OF DRAWINGS

FIGS. 3A-3E show the working principle of the CBSA-based, EATR-amplified fluorescence assay using DIS-CBSA-4536. (3A) FQ-DIS-4536-SF contains a fluorophore-quencher pair, and its fluorescence is quenched in the absence of target. (3B) In the presence of target, the CBSA assembles, (3C) creating a duplex that can be recognized and cleaved by Exo III at the abasic site (denoted by X). (3D) The complex then disassembles, releasing the intact long fragment, DIS-4536-LF, and target for additional rounds of complex formation and digestion. The fluorophore is also released and produces a signal, which (3E) becomes amplified over the course of many rounds of EATR.

FIGS. 4A-4C show the characterization of target-induced assembly of DIS-CBSA-4536, DIS-SA-36 (consisting of DIS-36-LF (SEQ ID No: 4) and FQ-DIS-36-SF (SEQ ID No: 5)), and DIS-SA-536 (consisting of DIS-536-LF (SEQ ID No: 6) and FQ-DIS-536-SF (SEQ ID No: 7)) using a fluorophore-quencher assay. (4A) Binding curves of these three split aptamers with DIS ranging from 0 to 5000 μM. Binding affinity ($K_{1/2}$) and cooperativity ($n_H$) was characterized by fitting with the Hill Equation. The error bars represent the standard deviation of three measurements. Structures of (4B) DIS-SA-36 and (4C) DIS-SA-536 are given.

FIGS. 5A-5C show Nupack predicted structures of (5A) DIS-4536-SF (SEQ ID No: 8), (5B) DIS-4536-LF, and (5C) DIS-CBSA-4536. Free energies are listed below each respective structure and the prevalence of each structure is listed above as a percentage.

FIGS. 6A-6C show the time-course of Exo III-mediated cleavage of DIS-CBSA-4536. (6A) Polyacrylamide gel electrophoresis (PAGE) analysis of digestion products from DIS-CBSA-4536. Reactions consisted of 1 μM DIS-4536-SF, 1 μM DIS-4536-LF and 0.004 U/μL Exo III with or without 500 μM DIS after 5, 10, 15, 30, 60, and 120 minutes of digestion. Cleavage of DIS-4536-SF (6B) and DIS-4536-LF (6C) was quantified by $(Int_0-Int)/Int_0 \times 100\%$, where $Int_0$ and Int are the band intensities of either fragment before and after the addition of Exo III, respectively.

FIGS. 7A-7C show digestion time-course of DIS-CBSA-4536 with excess DIS-SF. (7A) PAGE analysis of digestion products from 4 μM DIS-4536-SF and 1 μM DIS-4536-LF in the presence of 0.1 U/μL Exo III with or without 500 μM DIS after 10, 30, 60, 120, and 240 min of digestion. Digestion of DIS-4536-SF (7B) and DIS-4536-LF (7C) was quantified by $(Int_0-Int)/Int_0 \times 100\%$, where $Int_0$ and Int are the band intensities of either fragment before and after the addition of Exo III, respectively.

FIGS. 10A-10B show CBSA-based EATR-amplified fluorescence assay for sensitive detection of DIS in 50% urine using DIS-4536-LF and FQ-DIS-4536-SF. (10A) Calibration curve after a 30-min enzyme digestion with a linear range between 0 and 100 μM DIS (inset). (10B) Calibration curve at lower DIS concentrations. The signal gain was calculated from the fluorescence intensity of the samples. Error bars represent the standard deviation of three measurements.

FIGS. 11A-11D show the design of the cocaine-binding CBSA, COC-CBSA-5325, using a previously reported cocaine-binding aptamer (38-GC). (11A) 38-GC is truncated into (11B) two sets of short split aptamers (SSAs). (11C) Stem 1 of one SSA was merged with stem 2 of the other SSA and an abasic C3 spacer (denoted as X) was inserted to form (11D) COC-CBSA-5325, which consists of the short fragment COC-5325-SF (SEQ ID No: 9) and the long fragment COC-5325-LF (SEQ ID No: 10).

FIG. 15 shows the time-course digestion of the CBSA-cocaine complex characterized by 15% PAGE. Digestion involved 1 μM of COC-5325-LF and 1 μM COC-5325-SF by 0.01 U/μL Exo III with and without 250 μM cocaine. Digestion products were quantified by $(Int_0-Int)/Int_0 \times 100\%$, where $Int_0$ and Int are the band intensities of either fragment before and after the addition of Exo III, respectively.

FIGS. 16A-16B show the digestion of CBSAs consisting of modified versions of COC-5325-SF and COC-5325-LF characterized by 15% PAGE. (16A) Two-hour digestion of CBSAs consisting of 1 μM of COC-5325-SF and 1 μM of COC-5325-LF, COC-5325-LF-P (SEQ ID No: 17) or COC-5325-LF-B (SEQ ID No: 18) by 0.01 U/μL Exo III with or without 250 μM cocaine. (16B) Two-hour digestion of CBSAs consisting of 1 μM of COC-5325-LF-P and 1 μM of COC-5325-SF, COC-5325-SF-P (SEQ ID No: 19), or COC-5325-SF-B (SEQ ID No: 20) by 0.01 U/μL Exo III with and without 250 μM cocaine.

FIGS. 25A-25F show a colorimetric CBSA-based EATR-amplified assay for naked-eye detection of cocaine. (25A) AuNPs are coupled to the short fragment (SH-COC-5335-SF-1X) (SEQ ID No: 23), creating steric repulsion between AuNPs that produces a visible red color. (25B) Upon addition of long fragment (COC-5335-LF) and cocaine, the CBSA assembles, and the resulting duplexed abasic site can then (25C) be digested by Exo III. (25D) This cleaves off SH-COC-5335-SF-1X while recycling COC-5335-LF and cocaine for another round of assembly and digestion, until (25E) all short fragments have been sheared from the AuNP. (25F) These sheared AuNPs can now aggregate, producing a visible red-to-blue color change.

FIGS. 26A-26C show a cocaine-binding CBSA with a poly(A)$_5$-protected long fragment (COC-5335-LF-3'A) (SEQ ID No: 24) and different derivatives of COC-5335-SF such as (26A) COC-5335-SF-5'A (SEQ ID No: 25), (26B) COC-5335-SF-3'A (SEQ ID No: 26), and (26C) COC-5335-SF-T (SEQ ID No: 27). Arrows indicate suitable digestion sites for Exo III.

FIGS. 27A-27C show the time-course of CBSA digestion with COC-5335-SF-5'A. (27A) PAGE analysis of digestion products of CBSA consisting of 1 µM COC-5335-SF-5'A and 1 µM COC-5335-LF-3'A after treatment with 0.01 U/µL Exo III in the presence or absence of 250 µM cocaine for 5, 10, 15, 30, or 60 min of digestion. Digestion of (27B) COC-5335-SF-5'A and (27C) COC-5335-LF-3'A was quantified by $(Int_0-Int)/Int_0 \times 100\%$, where $Int_0$ and Int are the band intensities of either fragment before and after the addition of Exo III, respectively.

FIGS. 28A-28C show the time-course of CBSA digestion with COC-5335-SF-3'A. (28A) PAGE analysis of digestion products of CBSA consisting of 1 µM COC-5335-SF-3'A and 1 µM COC-5335-LF-3'A after treatment with 0.01 U/A Exo III in the presence or absence of 250 µM cocaine for 5, 10, 15, 30, or 60 min of digestion. Digestion of (28B) COC-5335-SF-3'A and (28C) COC-5335-LF-3'A was quantified by $(Int_0-Int)/Int_0 \times 100\%$, where $Int_0$ and Int are the band intensities of either fragment before and after the addition of Exo III, respectively.

FIGS. 29A-29C show time-course of CBSA digestion with COC-5335-SF-T. (29A) PAGE analysis of digestion products of CBSA consisting of 1 µM COC-5335-SF-T and 1 µM COC-5335-LF-3'A after treatment with 0.01 U/µL Exo III in the presence or absence of 250 µM cocaine for 5, 10, 15, 30 or 60 min of digestion. Digestion of (29B) COC-5335-SF-T and (29C) COC-5335-LF-3'A was quantified by $(Int_0-Int)/Int_0 \times 100\%$, where $Int_0$ and Int are the band intensities of either fragment before and after the addition of Exo III, respectively.

FIGS. 32A-32F show time-dependence of Exo III digestion of AuNPs displaying SH-COC-5335-SF-1X at (32A) 102±1, (32B) 41±1, (32C) 34±1, (32D) 25±1, or (32E) 22±1 strands/particle with 100 nM COC-5335-LF in the absence or presence of 250 µM cocaine. The detection window, during which the drug-containing sample is blue while the drug-free sample remains red, is marked as a vertical line. (32F) Summary of detection time and detection window obtained using AuNPs with different surface coverages.

FIGS. 33A-33F show alternative versions of the colorimetric cocaine sensor using SH-COC-5335-SF-2X (SEQ ID No: 28)-modified AuNPs.

FIGS. 34A-34B show surface coverage of SH-COC-5335-SF-2X-modified AuNPs treated with different concentrations of DTT. (34A) A standard calibration curve established with known concentrations of SH-COC-5335-SF-2X was used to calculate the DNA surface coverage of the DTT-treated AuNPs. (34B) The surface coverage decreased with increasing amounts of DTT employed during the treatment procedure. Error bars show standard deviations obtained from three measurements.

FIGS. 35A-35F show the time-dependence of Exo III digestion of AuNPs displaying SH-COC-5335-SF-2X at (35A) 83±2, (35B) 23±1, (35C) 20±1, (35D) 18±1, or (35E) 16±1 strands/particle with 100 nM COC-5335-LF in the absence or presence of 250 μM cocaine. The detection window, during which the drug-containing sample is blue while the drug-free sample remains red, is marked as a shaded box. (35F) Summary of detection time and detection window obtained using AuNPs with different surface coverages.

FIG. 36 shows the time-dependence of Exo III digestion of AuNPs modified with SH-COC-5335-SF-1X (25 strands/particle, black) or SH-COC-5335-SF-2X (20 strands/particle, red) in the absence (open circles and squares) or presence (solid circles and squares) of 250 μM cocaine.

FIGS. 37A-37B show an EATR-amplified CBSA-based assay for cocaine detection with SH-COC-5335-SF-2X-conjugated AuNPs and COC-5335-LF. (37A) After 20 minutes, samples containing cocaine at concentrations≥10 μM produced a clearly visible red to blue color change. Cocaine-free samples remained red. (37B) Calibration curve of our colorimetic CBSA-based cocaine assay; inset shows the calibration curve at low cocaine concentrations.

FIG. 38 shows the specificity of the EATR-amplified CBSA-based colorimetric assay with SH-COC-5335-SF-2X-conjugated AuNPs with COC-5335-LF for 50 μM cocaine versus various interferents. A red-to-blue color change was observed in the cocaine sample, whereas lidocaine, caffeine, levamisole, and benzocaine samples remained red after 20 minutes of digestion.

BRIEF DESCRIPTION OF SEQUENCES

Figure 1:
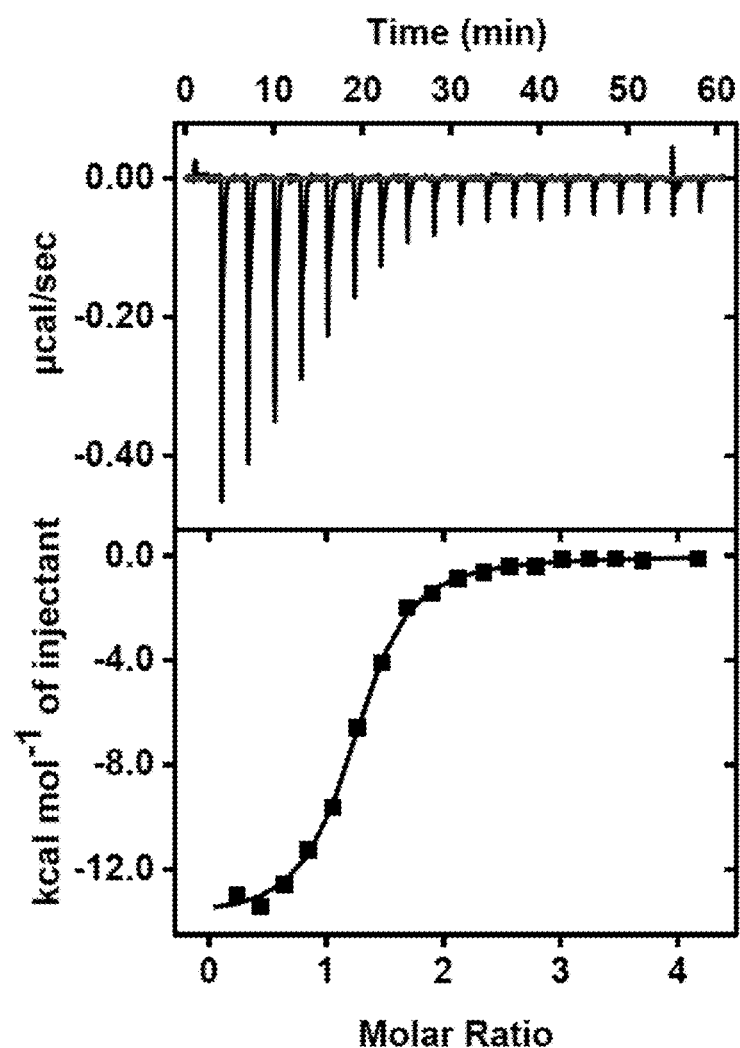
FIG. 1 shows characterization of DIS binding affinity of the single-stranded DIS binding aptamer DISS.1-AT (SEQ ID No: 1) using isothermal titration calorimetry (ITC). The top panel presents raw data showing the heat generated from each titration of DIS to DISS.1-AT. The bottom panel shows the integrated heat of each titration after correcting for dilution heat of the titrant.

SEQ ID NO: 1 is the sequence of a DIS-binding aptamer DISS.1-AT contemplated for use according to the subject invention.

SEQ ID NO: 2 is the sequence of a long fragment of DIS-binding CBSA modified with a 3' poly $(A)_5$ extension contemplated for use according to the subject invention.

SEQ ID NO: 3 is the sequence of a short fragment of DIS-binding CBSA, which is modified with a fluorophore-quencher pair, an abasic site, and a 3' poly $(A)_5$ extension contemplated for use according to the subject invention.

SEQ ID NO: 4 is the sequence of a long fragment of DIS-binding split aptamer modified with a 3' poly $(A)_5$ extension contemplated for use according to the subject invention.

SEQ ID NO: 5 is the sequence of a short fragment of DIS-binding split aptamer modified with a fluorophore-quencher pair and a 3' poly $(A)_5$ extension contemplated for use according to the subject invention.

SEQ ID NO: 6 is the sequence of a long fragment of DIS-binding split aptamer modified with a 3' poly $(A)_5$ extension contemplated for use according to the subject invention.

SEQ ID NO: 7 is the sequence of a short fragment of DIS-binding split aptamer, which is modified with a fluorophore-quencher pair, an abasic site, and a 3' poly $(A)_5$ extension contemplated for use according to the subject invention.

SEQ ID NO: 8 is the sequence of a short fragment of DIS-binding CBSA modified with an abasic site and a 3' poly $(A)_5$ extension contemplated for use according to the subject invention.

SEQ ID NO: 9 is the sequence of a long fragment of cocaine-binding CBSA contemplated for use according to the subject invention.

SEQ ID NO: 10 is the sequence of a short fragment of cocaine-binding CBSA modified with an abasic site contemplated for use according to the subject invention.

SEQ ID NO: 11 is the sequence of a long fragment of cocaine-binding CBSA contemplated for use according to the subject invention.

SEQ ID NO: 12 is the sequence of a short fragment of cocaine-binding CBSA modified with an abasic site contemplated for use according to the subject invention.

SEQ ID NO: 13 is the sequence of a long fragment of cocaine-binding CBSA contemplated for use according to the subject invention.

SEQ ID NO: 14 is the sequence of a short fragment of cocaine-binding CBSA modified with an abasic site contemplated for use according to the subject invention.

SEQ ID NO: 15 is the sequence of a long fragment of cocaine-binding CBSA contemplated for use according to the subject invention.

SEQ ID NO: 16 is the sequence of a short fragment of cocaine-binding CBSA modified with an abasic site contemplated for use according to the subject invention.

SEQ ID NO: 17 is the sequence of a long fragment of cocaine-binding CBSA modified with a 3' poly $(T)_5$ extension contemplated for use according to the subject invention.

SEQ ID NO: 18 is the sequence of a long fragment of cocaine-binding CBSA modified with a single 3' inverted deoxythymidine contemplated for use according to the subject invention.

SEQ ID NO: 19 is the sequence of a short fragment of cocaine-binding CBSA, which is modified with an abasic site and a 3' poly $(T)_5$ extension, contemplated for use according to the subject invention.

SEQ ID NO: 20 is the sequence of a short fragment of cocaine-binding CBSA, which is modified with an abasic site and a single 3' inverted deoxythymidine, contemplated for use according to the subject invention.

SEQ ID NO: 21 is the sequence of a short fragment of cocaine-binding CBSA, which is modified with a fluorophore-quencher pair, an abasic site, and a single 3' inverted deoxythymidine, contemplated for use according to the subject invention.

SEQ ID NO: 22 is the sequence of a long fragment of cocaine-binding CBSA modified with a 3' poly $(T)_{18}$ extension contemplated for use according to the subject invention.

SEQ ID NO: 23 is the sequence of a thiolated short fragment of cocaine-binding CBSA modified with an abasic site and a 5' poly $(T)_5$ extension contemplated for use according to the subject invention.

SEQ ID NO: 24 is the sequence of a long fragment of cocaine-binding CBSA modified with a 3' poly $(A)_5$ extension contemplated for use according to the subject invention.

SEQ ID NO: 25 is the sequence of a short fragment of cocaine-binding CBSA, which is modified with an abasic site and a 5' poly $(A)_5$ extension, contemplated for use according to the subject invention.

SEQ ID NO: 26 is the sequence of a short fragment of cocaine-binding CBSA, which is modified with an abasic site and a 3' poly $(A)_5$ extension, contemplated for use according to the subject invention.

SEQ ID NO: 27 is sequence of a short fragment of cocaine-binding CBSA in which the abasic site is replaced with deoxythymidine contemplated for use according to the subject invention.

SEQ ID NO: 28 is the sequence of two tandem abasic-site-incorporated, thiolated short fragment repeats with an internal $(T)_6$ linker and a 5' poly $(T)_5$ extension contemplated for use according to the subject invention.

DETAILED DESCRIPTION

The subject invention provides methods, assays, and products for detecting small molecules in a sample, in particular, in both clinical and field settings. In one embodiment, the method for detecting a small-molecule target in a sample comprises providing a sample, contacting the sample with an aptamer-based sensor selective for the small-molecule target, and detecting the small-molecule target in the sample.

In one embodiment, the detection of the small-molecule target comprises measuring a signal generated upon assembly of the aptamer-target complex. In another embodiment, the method further comprises determining the concentration of the small-molecule target in the sample.

The term "small molecule," or "small-molecule target," as used herein, includes any molecule capable of being detected using an aptamer technique. In one embodiment, the small-molecule target may be an amino acid, an amino acid-related molecule, a peptide, a steroid, a lipid, a sugar, a carbohydrate, a biomarker, a drug molecule, a drug metabolite, a coenzyme, a nucleotide, a nucleotide-related molecule, a pyridine nucleotide, a cyclic nucleotide, or a cyclic dinucleotide. In other embodiments, the small-molecule target may be an infective agent, antigen, toxin, disease biomarker, or a specific metal ion.

In one embodiment, the small molecule is a steroid hormone. In a specific embodiment, the steroid hormone is dehydroisoandrosterone-3-sulfate (DIS).

In another embodiment, the small molecule is a drug molecule. In a specific embodiment, the drug molecule is cocaine or cocaine derivative. Cocaine derivative may or may not have the core structure of cocaine. Exemplary cocaine derivatives include, but are not limited to, 4-fluorococaine, 2-hydroxycocaine, 3-(p-fluorobenzoyloxy)tropane (pFBT), procaine, and dimethocaine.

The subject invention provides aptamer-based sensors for detecting small-molecule targets. Aptamers are nucleic acid molecules characterized by the ability to bind to a target molecule with high specificity and high affinity. Almost every aptamer identified to date is a non-naturally occurring molecule. Aptamers to a given target may be identified and/or produced by the method of SELEX.

In one embodiment, the aptamer may be an oligonucleotide, such as a DNA or RNA molecule and may be single stranded or double stranded. Preferably, the aptamer is single stranded. They may form various secondary structures (e.g., stems, loops, bulges, pseudoknots, G-quadruplexes and kissing hairpins), which in turn can form unique three-dimensional architectures able to specifically recognize their targets by exploiting a variety of interactions—such as hydrophobic and electrostatic interactions, hydrogen bonding, van der Waals forces, and $\pi$-$\pi$ stacking as well as shape complementarity.

As used herein, the terms "polynucleotide," "nucleotide," "oligonucleotide," and "nucleic acid" can be used interchangeably to refer to a nucleic acid comprising DNA, RNA, derivatives thereof, or combinations thereof.

In another embodiment, the aptamer is a split aptamer, e.g., an aptamer is split into two, three or more pieces, which re-associate in the presence of a target ligand. The use of a split aptamer offers distinct advantages for sensor development over other aptamers, e.g., structure-switching aptamers, as the only requirement is that the split aptamer binds its target. In a preferred embodiment, the aptamer is a DNA split aptamer.

In one embodiment, each piece of the split aptamer according to the present invention may have a minimum length of, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. Each piece of the split aptamer according to the present invention may have a maximum length of, for example, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides. Each piece of the split aptamer according to the present invention may have a length of, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

In one embodiment, the split aptamer comprises at least one stem, two stems, or three stems. Preferably, the aptamer comprises three stems. Each stem may be fully or partially complementary. Each stem may comprise the same or a different number of nucleotides. Exemplary lengths of each stem may be, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides.

In one embodiment, the split aptamer comprises at least one junction, which is formed when two or more stems meet. In certain embodiments, the junction may be a loop between two stems, or a three-way junction (TWJ). The junction may comprise, for example, 5, 6, 7, 8, 9, 10, 11, 12, 13, 14, 15, 16, 17, 18, 19, 20, 21, 22, 23, 24, 25, 26, 27, 28, 29, or 30 nucleotides. The junction in an aptamer can serve as a binding domain for a small-molecule target. In specific embodiments, the split aptamer comprises one TWJ-binding domain. In some embodiments, the split aptamer may be a monomer, dimer, trimer, or tetramer. Such aptamer can comprise one, two, three, or four TWJ-binding domains.

In one embodiment, the aptamer-based sensor is a cooperative binding split aptamer (CBSA). CBSAs can be engineered from parent split aptamers comprising a single target-binding domain and consist of a short fragment and a long fragment that contain two target-binding domains. Advantageously, CBSAs with two target-binding domains exhibit enhanced target response compared with single-domain split aptamers. The first binding event partially stabilizes the CBSA and facilitates the second binding event. This cooperative assembly can reduce the target concentration required to assemble the CBSA several-fold, resulting in far greater specificity and sensitivity relative to the parent split aptamer.

In one embodiment, each fragment of CBSA according to the present invention may have a minimum length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. Each fragment of CBSA according to the present invention may have a maximum length of, for example, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides. Each fragment of CBSA according to the present invention may have a length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

The CBSAs according to the present invention may comprise at least 10, at least 20, at least 30, at least 40, at least 50, at least 60, at least 70, or at least 80 nucleotides. The CBSAs according to the present invention may comprise at most about 200 nucleotides, at most about 150 nucleotides, at most about 120 nucleotides, at most about 100 nucleotides, at most about 90 nucleotides, at most about 80 nucleotides, at most about 70 nucleotides, at most about 60 nucleotides, or at most about 50 nucleotides. The aptamer according to the present invention comprises, for example, in the range of 10 to 200 nucleotides, preferably 15 to 150 nucleotides, more preferably 20 to 100 nucleotides.

In one embodiment, the subject invention provides a method for generating a CBSA selective for a small-molecule target, comprising producing a parent split aptamer selective for the small-molecule target, and generating the CBSA by merging two of the parent split aptamers, wherein the parent split aptamer comprises a first piece of the split aptamer and a second piece of the split aptamer, and wherein the parent split aptamer comprises a single binding domain for the small-molecule target.

In one embodiment, the parent split aptamer may be generated by the steps of 1) providing a first piece of a split aptamer and a second piece of the split aptamer, wherein the first piece and the second piece of the split aptamer form a single-domain split aptamer in the presence of a small-molecule target, wherein the single-domain split aptamer comprises a first stem, a second stem and a third stem, 2) removing a number of base pairs in at least one of the stems selected from the first stem, the second stem and the third stem, and 3) removing a loop region of the single-domain split aptamer.

In a further embodiment, the parent split aptamer may be generated by the steps of 1) providing a first piece of a split aptamer and a second piece of the split aptamer, wherein the first piece and the second piece of the split aptamer form a single-domain split aptamer in the presence of a small-molecule target, wherein the single-domain split aptamer comprises a first stem, a second stem and a third stem, 2) removing a number of base pairs in the first stem, and 3) removing a loop region of the single-domain split aptamer, wherein the loop region is a poly(T)n loop region (n>2).

In some embodiments, the aptamers/split aptamers/CBSAs may each independently have free ends. For example, the 3' and 5' ends may not be ligated to form a loop, although they may be conjugated to other molecules or otherwise modified. The aptamers/split aptamers/CBSAs according to the subject invention may each independently adopt a tertiary structure such as a hairpin loop. In some embodiments, the aptamers/split aptamers/CBSAs according to the subject invention may each independently be looped. For example, the 5' and 3' ends of the nucleic acid are covalently bonded, e.g. by ligation, to form a loop not having any free ends.

The aptamers/split aptamers/CBSAs of the present invention may or may not include chemical modifications as described herein such as a chemical substitution at a sugar position, a phosphate position, and/or a base position of the nucleic acid including, for example, incorporation of a modified nucleotide, incorporation of a capping moiety (e.g., 3' capping), conjugation to a high molecular weight, non-immunogenic compound (e.g., polyethylene glycol (PEG)), conjugation to a lipophilic compound, and substitutions in the phosphate backbone. Base modifications may include 5-position pyrimidine modifications, modifications at exocyclic amines, substitution of 4-thiouridine, substitution of 5-bromo- or 5-iodo-uracil, and backbone modifications. Sugar modifications may include 2'-amine nucleotides (2'-NH2). 2'-fluoronucleotides (2'-F), and 2'-O-methyl (2'-OMe) nucleotides. Such modifications may improve the stability of the aptamers/split aptamers/CBSAs or make the aptamers/split aptamers/CBSAs more resistant to degradation. In some embodiments, each base of a given type (e.g., A, T, C, and G) may contain the same chemical modification.

The aptamers/split aptamers/CBSAs may be modified by addition of one or more reporter labels (or detectable labels). In some embodiments, the label may be attached to either the 5' or 3' end of the aptamer/split aptamer/CBSA. The label may also be attached with the backbone of the aptamer/split aptamer/CBSA. The skilled person will be aware of techniques for attaching labels to nucleic acid strands. The detectable label may be attached directly or indirectly to the nucleic acid aptamer. If the label is indirectly attached to the nucleic acid aptamer, it may be by any mechanism known to one of skill in the art, such as using biotin and streptavidin.

In one embodiment, the aptamers/split aptamers/CBSAs may comprise a reporter label, such as a fluorescent dye, nanoparticle, or an enzyme. Exemplary labels include, but not limited to, an organic donor fluorophore or an organic acceptor fluorophore, a luminescent lanthanide, a fluorescent or luminescent nanoparticle, an affinity tag such as biotin, or a polypeptide. In some embodiments, the aptamer may comprise a fluorescent label, for example, 2-amino-5,6,7-trimethyl-1,8-naphthyridine (ATMND), fluorescein, TAMRA, rhodamine, Texas Red, Alexa Fluor (e.g., AlexaFluor 488, AlexaFluor 532, AlexaFluor 546, AlexaFluor 594, AlexaFluor 633 and AlexaFluor 647), cyanine dye (e.g., Cy5, Cy5.5 and Cy3), Tye dye (e.g., TYE 563, TYE 665, TYE 705), atto dye (e.g., Atto 594 and Atto 633), Hexachlorofluorescein, FAM (6-carboxyfluroescein), BODIPY FL, OliGreen, 40, 6-diamidino-2-phenylindol (DAPI), Hoechst 33,258, malachite green (MG), and FITC. The nanoparticle can be an upconversion nanoparticle. In some embodiments, the fluorophore is selected from the group consisting of fluorophores that emit a blue, green, near red, or far red fluorescence.

In one embodiment, the reporter label is a fluorescent dye and quencher pair. In certain embodiments, a fluorophore is conjugated at one end of the short fragment of CBSAs and a quencher at the other end of the short fragment of CBSAs. In the absence of its target, the short fragment of the CBSA is folded into a hairpin conformation, thereby positioning the fluorophore close to the quencher. Upon target binding, base-pairing in the hairpin is interrupted and the CBSA converts to its open conformation, in which the fluorophore and the quencher do not interact. The resulting recovery of the fluorescence signal directly reflects the extent of the binding and can be used for detection and quantitative measurement of the target concentration.

The quenchers can be, for example, Dabcyl, DDQ-I, Eclipse, Iowa Black FQ, BHQ-1, QSY-7, BHQ-2, DDQ-II, Iowa Black RQ, QSY-21, or BHQ-3.

In some embodiments, the fluorophore is at a location of, for example, $1^{st}$, $2^{nd}$, $3^{th}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$ or $20^{th}$ nucleotide from either 5' end or 3' end of the short fragment of the CBSAs. The quencher is at a location of, for example, $1^{st}$, $2^{nd}$, $3^{th}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, or $20^{th}$ nucleotide from either 3' end or 5' end of the short fragment of the CBSAs.

It is contemplated that the location of the fluorophore and quencher-conjugated short fragment is such that the proximity of fluorophore and quencher in a hairpin conformation provide maximal quenching and the fluorophore and quencher in an open conformation provide maximal fluorescence of the fluorophore. For optimized detection of fluorescence changes that allows utilization of the CBSAs for target detection, it is desirable that the fluorescence in the quenched conformation is as low as possible and the fluorescence in the unquenched conformation is as high as possible combined with the most rapid interconversion from one conformation to the other.

In one embodiment, the CBSA-target complex may produce a time resolved fluorescence energy transfer (TR-FRET) signal or a signal that can be measured by fluorescence polarization (FP), and/or luminescence.

In one embodiment, the subject invention provides methods for detecting a small-molecule target in a sample using CBSAs, comprising contacting the sample with a CBSA selective for the small-molecule target to form a CBSA-target complex, and detecting the small-molecule target in the sample by measuring a signal generated upon assembly of the CBSA-target complex.

In some embodiments, the signal generated upon assembly of the CBSA-target complex has optical properties selected from the group consisting of: light reflectivity, color, the fluorescence emission wavelength(s) and the fluorescence emission intensity.

In specific embodiments, the 3' end of the short fragment or the long fragment of the CBSAs is conjugated with a fluorophore, such as Cy5, and the 5' end of the short fragment or the long fragment of the CBSAs is conjugated with a quencher, such as Iowa Black RQ. The fluorescence emission change is indicative of the binding of CBSAs with the small molecules and the detection of such small molecules in the sample.

In one embodiment, the CBSA may comprise a cleavage site of a chemical or enzymatic reaction within the short fragment or the long fragment. In a further embodiment, the cleavage site is an abasic site which can be a natural or synthetic abasic site. The abasic site may be positioned in a phosphodiester backbone shortened by 1-carbon atom or duplexes where phosphorothioate replaces the phosphate group 5' to the abasic site. In some embodiments, the cleavage site is a duplexed nucleotide containing modifications including, but not limited to, a 2'dexoyribose, 2'-deoxyribosylformamide, tetrahydrofuranyl, ethanyl, or propanyl (C3 spacer) group.

In one embodiments, the cleavage site can be cleaved by, for example, nucleases (e.g., exonucleases, and endonucleases), and DNAzymes. The nucleases include, but not limited to, endonuclease IV, apurinic/apyrimidinic endonuclease, or exonuclease III (Exo III).

In a specific embodiment, the cleavage site is a C3 spacer abasic site, which can be recognized and cleaved by Exo III. The duplexed C3 spacer abasic site is introduced between the two binding domains in the short fragment or the long fragment.

Advantageously, the cleavage of the short fragment containing a duplexed C3 spacer abasic site of the CBSA results in disassembly of the CBSA-target complex, releasing the long fragment, the small-molecule target, and the fluorophore that now fluoresces due to its separation from the quencher. The released long fragment and small-molecule target are then free to assemble with another short fragment of the CBSA, enabling EATR signal amplification. On the other hand, the cleavage of the long fragment containing a duplexed C3 spacer abasic site of the CBSA results in disassembly of the CBSA-target complex, releasing the short fragment, the small-molecule target, and the fluorophore that now fluoresces due to its separation from the quencher. The released short fragment and small-molecule target are free to assemble with another long fragment of the CBSA, enabling EATR signal amplification. As a result, a very small amount of target molecules can be recycled for multiple rounds of assembly and cleavage, thereby generating a substantially amplified fluorescence signal.

In one embodiment, the subject invention provides an approach for the development of rapid and sensitive EATR-amplified small-molecule sensors based on CBSAs. The CBSA-based EATR-amplified sensor for detecting a small-molecule target in a sample comprises a short fragment of a CBSA and a long fragment of the CBSA, wherein the short fragment of the CBSA comprises an enzyme cleavage site, wherein the short fragment of the CBSA and the long fragment of the CBSA are assembled in the presence of the small-molecule target to form a CBSA-target complex. In some embodiments, the CBSAs may comprise a fluorescent dye, or nanoparticle (e.g., AuNP) at the end of either the short fragment or the long fragment, preferably, at the end of the short fragment of CBSAs. In a further embodiment, the sensor also comprises an enzyme that recognizes and cleaves abasic sites including, but not limited to, 2'dexoyribose, 2'-deoxyribosylfoanamide, tetrahydrofuranyl, propanyl, and ethanyl sites. In a preferred embodiment, the cleavage site is a duplexed C3 spacer abasic site, and the enzyme that recognizes and cleaves the abasic site is Exo III.

In one embodiment, the CBSA according to the subject invention comprises a long fragment selected from SEQ ID NO: 2, SEQ ID NO: 9, SEQ ID NO: 11, SEQ ID NO: 13, SEQ ID NO: 15, SEQ ID NO: 17, SEQ ID NO: 18, SEQ ID NO: 22, and SEQ ID No:24; or a sequence sharing at least 50%, 55%, 60%, 65%, 70%, 75%, 80%, 85%, 90%, 95% or 99% identity with SEQ ID No: 2, SEQ ID NO: 9, SEQ ID NO: 11, SEQ ID NO: 13, SEQ ID NO: 15, SEQ ID NO: 17, SEQ ID NO: 18, SEQ ID NO: 22, or SEQ ID No:24.

In one embodiment, the CBSA according to the subject invention comprises a short fragment selected from SEQ ID NO: 3, SEQ ID NO: 8, SEQ ID NO: 10, SEQ ID NO: 12, SEQ ID NO: 14, SEQ ID NO: 16, SEQ ID NO: 19, SEQ ID NO: 20, SEQ ID NO: 21, SEQ ID NO: 23, SEQ ID NO: 25, SEQ ID No:26, SEQ ID NO: 27 and SEQ ID NO: 28; or a sequence sharing at least 50%, 55%, 60%, 65%, 70%, 75%, 80%, 85%, 90%, 95% or 99% identity with SEQ ID NO: 3, SEQ ID NO: 8, SEQ ID NO: 10, SEQ ID NO: 12, SEQ ID NO: 14, SEQ ID NO: 16, SEQ ID NO: 19, SEQ ID NO: 20, SEQ ID NO: 21, SEQ ID NO: 23, SEQ ID NO: 25, SEQ ID No:26, SEQ ID NO: 27 or SEQ ID NO: 28.

In one embodiment, the subject invention provides a method for detecting a small-molecule target in a sample employing CBSAs as EATR-amplified sensors. Advantageously, the methods utilizing CBSA-based, EATR-amplified assays are rapid, sensitive, and specific for the detection of various small-molecule targets.

In one embodiment, the subject invention provides methods for detecting small-molecule targets using EATR-amplified sensors, comprising contacting the sample with an EATR-amplified sensor selective for the small-molecule target, and detecting the small-molecule target in the sample. In a further embodiment, the detection of the small-molecule target comprises measuring a signal generated upon assembly and cleavage of CBSA-target complex in the EATR-amplified sensor.

In one embodiment, the EATR-amplified sensor is a CBSA comprising an enzyme cleavage site in the short fragment, a fluorophore conjugated at the 3' end of the short fragment, and a quencher conjugated at the 5' end of the short fragment. In another embodiment, the EATR-amplified sensor is a CBSA comprising an enzyme cleavage site in the long fragment, a fluorophore conjugated at the 3' end of the long fragment, and a quencher conjugated at the 5' end of the long fragment.

In one embodiment, the EATR-amplified sensor is a CBSA comprising an enzyme cleavage site in the short fragment, a fluorophore conjugated at the 5' end of the short fragment, and a quencher conjugated at the 3' end of the short fragment. In another embodiment, the EATR-amplified sensor is a CBSA comprising an enzyme cleavage site in the long fragment, a fluorophore conjugated at the 5' end of the long fragment, and a quencher conjugated at the 3' end of the long fragment.

In a preferred embodiment, the fluorophore is Cy5 and the quencher is Iowa Black RQ. In a preferred embodiment, the cleavage site is a duplexed C3 spacer abasic site, and the enzyme that recognizes and cleaves the abasic site is Exo III.

In one embodiment, the method further comprises determining the concentration of the small-molecule target in the sample. The determination can comprise comparing the fluorescent signal generated upon binding of target and cleavage of the CBSA-target complex in the EATR-amplified sensor with a standard calibration curve of the fluorescence signal of the fluorophore in the presence of various concentrations of the small-molecule target.

In one embodiment, the subject invention provides an instrument-free colorimetric assay employing EATR-mediated aggregation of CBSA-modified gold nanoparticles (AuNPs) for the rapid detection of small molecules at very low concentration. This sensor utilizes CBSA-conjugated AuNPs and EATR amplification for visual detection of the small molecules. The sensor comprises a short fragment of a CBSA and a long fragment of the CBSA, wherein the short fragment of the CBSA comprises an enzyme cleavage site within the backbone of the short fragment, wherein an end of the short fragment of the CBSA is conjugated to an AuNP, and wherein the short fragment of the CBSA and the long fragment of the CBSA are associated in the presence of the small-molecule target to form a CBSA-target complex.

In the presence of target, the fragments assemble to form CBSA-target complexes on the nanoparticle surface. The enzyme specifically recognizes the cleavage site between the two binding domains and cleaves the AuNP-conjugated short fragment, releasing the intact long fragment and target molecule for another round of target assembly and enzyme cleavage. Once all of the short fragments have been cleaved from the particle surface, the AuNPs aggregate and produce a visible red-to-blue color change. In contrast, in the absence of target, the intact short fragments of CBSA prevent AuNP aggregation such that the color remains red.

In one embodiment, the nanoparticle, such as AuNP, used in the method according to the subject invention has a size from about 1 nm to about 100 nm, about 1 nm to about 90 nm, about 1 nm to about 80 nm, about 1 nm to about 70 nm, about 1 nm to about 60 nm, about 1 nm to about 50 nm, about 1 nm to about 40 nm, about 1 nm to about 30 nm, about 1 nm to about 20 nm, about 1 nm to about 10 nm, about 1 nm to about 9 nm, about 1 nm to about 8 nm, about 1 nm to about 7 nm, about 1 nm to about 6 nm, or about 1 nm to about 5 nm. In specific embodiments, the AuNP used in the method according to the subject invention has a size of 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, or 50 nm.

In some embodiments, the nanoparticle (e.g., AuNP) may have more than two short fragments of CBSAs conjugated to its surface. In other embodiments, the surface of a nanoparticle (e.g., AuNP) may be conjugated with CBSA, preferably, the short fragments of the CBSAs, at a range of 2 to 500 strands/particle, 5 to 400 strands/particle, 10 to 300 strands/particle, or 15 to 200 strands/particle. In certain embodiments, the surface of a nanoparticle (e.g., AuNP) may be conjugated with CBSA, preferably, the short fragments of the CBSAs, at a number of, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 strands/particle.

In one embodiment, the short fragments of CBSAs may be arranged in repeat through a linker. The repeat of short fragments of CBSAs may be connected through the linker prior to, during, or after the reassociation with the long fragments of CBSAs. In one embodiment, the repeat of short fragment may comprise at least two, at least three, at least four, at least five, or at least six repeats. In another embodiment, the repeat of short fragment may comprise two, three, four, five, or six short fragments. These repeats may be connected in series through linkers. In one embodiment, the linker is a $(T)_n$ linker, n>2. In a preferred embodiment, the linker is a $(T)_6$ linker. In another embodiment, these short fragments may each independently comprise the same or different modifications. In a further embodiment, the short fragment repeats comprise an abasic site incorporated in each short fragment. In a specific embodiment, the short fragment repeat has a sequence of SEQ ID No: 28 (i.e., SH-COC-5335-SF-2X) comprising of two tandem abasic-site-incorporated short fragment repeats with a $(T)_6$ linker, or a sequence sharing at least 50%, 55%, 60%, 65%, 70%, 75%, 80%, 85%, 90%, 95% or 99% identity with SEQ ID No: 28.

In one embodiment, the method according to the subject invention can achieve superior sensitivity for target detection at low micromolar or nanomolar concentration, for example, as low as 200 μM, 100 μM, 10 μM, 1 μM, 100 nM, 10 nM, or 1 nM. In a specific embodiment, the method according to the subject invention can achieve target sensitivity at a low concentration of 1 μM.

Advantageously, the methods for small molecule detection provided herein are rapid and can be completed in about 5 minutes to about 120 minutes, about 6 minutes to about 110 minutes, about 7 minutes to about 100 minutes, about 8 minutes to about 90 minutes, about 9 minutes to about 80 minutes, about 10 minutes to about 70 minutes about 15 minutes to about 60 minutes, about 20 minutes to about 50 minutes, or about 25 minutes to about 40 minutes. In some embodiments, the method can be completed in about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, or about 120 minutes.

In one embodiment, the CBSA-based EATR-amplified sensors may be used in a high throughput setting for detecting small molecules.

In one embodiment, the small molecule is a steroid hormone. In a specific embodiment, the steroid hormone is dehydroisoandrosterone-3-sulfate (DIS).

In another embodiment, the small molecule is a drug molecule. In a specific embodiment, the drug molecule is cocaine, a cocaine derivative or a cocaine analog. Cocaine derivatives may be synthesized compounds that mimic the structure of the cocaine, either with or without a tropane ring, for example, 4-fluorococaine, 2-hydroxycocaine, 3-(p-fluorobenzoyloxy)tropane (pFBT), and dimethocaine. Cocaine analog may include compounds that are antagonists of the effects of cocaine, or that are agonists of cocaine-binding receptors.

In one embodiment, the sample may be a biological sample such as blood, plasma, sweat, urine, tears, or saliva of a subject. The subject may be any animal or human, preferably, human. The subjects may also refer to any animal including, but not limited to, non-human primates, rodents, dogs, cats, horses, cattle, pigs, sheep, goats, chickens, guinea pigs, hamsters and the like.

In one embodiment, the subject invention provides a method for detecting DIS in a sample comprising contacting the sample with an aptamer selective for DIS, and detecting DIS in the sample.

In one embodiment, the subject invention provides a method for detecting DIS in a biological sample comprising contacting the sample with a CBSA selective for DIS, wherein the CBSA and DIS form a CBSA-DIS complex, and detecting DIS in the biological sample by measuring a signal generated upon assembly of the CBSA-DIS complex. In a specific embodiment, the signal generated upon assembly of the CBSA-DIS complex may be a change in the fluorescence intensity.

In one embodiment, the subject invention provides a method for detecting DIS in a biological sample using CBSA-based EATR-amplified fluorescence and colorimetric assays. The method comprises providing a biological sample, contacting the biological sample with an EATR-amplified sensor selective to DIS, and detecting DIS in the biological sample by measuring a signal generated upon assembly and cleavage of the CBSA-DIS complex in the EATR-amplified sensor.

In a further embodiment, the EATR-amplified sensors is a CBSA comprising an enzyme cleavage site in the short fragment, a fluorophore conjugated at the 3' end of the short fragment, and a quencher conjugated at the 5' end of the short fragment. In a preferred embodiment, the fluorophore is Cy5 and the quencher is Iowa Black RQ. In a preferred embodiment, the cleavage site is a duplexed C3 spacer abasic site, and the enzyme that recognizes and cleaves the abasic site is Exo III.

In specific embodiments, the long fragment of CBSA is DIS-4536-LF according to SEQ ID No: 2 or a sequence sharing at least 50%, 55%, 60%, 65%, 70%, 75%, 80%, 85%, 90%, 95% or 99% identity with SEQ ID No: 2. The short fragment of CBSA is FQ-DIS-4536-SF according to SEQ ID No: 3 or a sequence sharing at least 50%, 55%, 60%, 65%, 70%, 75%, 80%, 85%, 90%, 95% or 99% identity with SEQ ID No: 3.

In a preferred embodiment, the CBSA selective for DIS is DIS-CBSA-4536.

The method can further comprise introducing Exo III in the sample, resulting in recycling of the long fragment and DIS molecules for further rounds of detection, while releasing a fluorescent signal for each detection event.

In a preferable embodiment, the biological sample is a urine sample. Advantageously, this method can achieve 100-fold enhanced target sensitivity relative to a non-EATR-based method. The detection limit of the CBSA-based EATR-amplified fluorescence assay is 100 and 50 times lower than previously reported DIS assays based on a split aptamer and a structure-switching aptamer, respectively. This method also allows the detection of DIS in 50% urine within 30 minutes at concentrations as low as 1 µM.

In one embodiment, the subject invention provides a method for detecting cocaine in a sample comprising contacting the sample with an aptamer selective for cocaine, and detecting cocaine in the sample.

In one embodiment, the subject invention provides a method for detecting cocaine in a biological sample comprising contacting the biological sample with a CBSA selective for cocaine, wherein the CBSA and cocaine form a CBSA-cocaine complex, and detecting cocaine in the biological sample by measuring a signal generated upon assembly of the CBSA-cocaine complex. In a specific embodiment, the signal generated upon assembly of the CBSA-cocaine complex may be the changes in the fluorescence intensity.

In one embodiment, the subject invention provides a method for detecting cocaine in a biological sample using CBSA-based EATR-amplified fluorescence and colorimetric assays. The method comprises providing a biological sample, contacting the biological sample with an EATR-amplified sensor selective for cocaine, and detecting cocaine in the biological sample by measuring a signal generated upon assembly and cleavage of the CBSA-cocaine complex in the EATR-amplified sensor.

In another embodiment, the EATR-amplified sensors selective for cocaine is a CBSA comprising a short fragment and a long fragment, wherein the short fragment comprises an enzyme cleavage site that can be recognized and bound by a fluorescent dye. In a preferred embodiment, the fluorescent dye is ATMND. In a specific embodiment, the cleavage site is a duplexed C3 spacer abasic site, and the enzyme that recognizes and cleaves the abasic site is Exo III.

In a preferred embodiment, the long fragment is COC-5325-LF according to SEQ ID: 9 or a sequence sharing at least 50%, 55%, 60%, 65%, 70%, 75%, 80%, 85%, 90%, or 95% identity with SEQ ID No: 9. The short fragment is COC-5325-SF according to SEQ ID No: 10 or a sequence sharing at least 50%, 55%, 60%, 65%, 70%, 75%, 80%, 85%, 90%, 95% or 99% identity with SEQ ID No: 10.

In another embodiment, the EATR-amplified sensors selective for cocaine is a CBSA comprising a short fragment and a long fragment, wherein the short fragment comprises an enzyme cleavage site within the backbone, wherein an end of the short fragment is conjugated to an AuNP, and wherein the short fragment and the long fragment are associated in the presence of cocaine to form a CBSA-target complex.

In a preferred embodiment, the long fragment is COC-5335-LF according to SEQ ID No:11 or a sequence sharing at least 50%, 55%, 60%, 65%, 70%, 75%, 80%, 85%, 90%, or 95% identity with SEQ ID No: 11. The short fragment is SH-COC-5335-SF-2X according to SEQ ID No: 28 or a sequence sharing at least 50%, 55%, 60%, 65%, 70%, 75%, 80%, 85%, 90%, 95% or 99% identity with SEQ ID No: 28.

In another embodiment, the short fragment is a derivative of COC-5335-SF. In some embodiments, the derivative can include a poly(A)$_5$ extension at the 5' end that allows digestion of both the abasic site and the 3' terminus, or at the 3' instead of 5' end, allowing cleavage only at the abasic site. In a specific embodiment, the derivative may comprise a thymine.

In specific embodiment, the derivative is COC-5335-SF-5'A according to SEQ ID No: 25, COC-5335-SF-3'A according to SEQ ID No: 26, COC-5335-SF-T according to SEQ ID No: 27 or a sequence sharing at least 50%, 55%, 60%, 65%, 70%, 75%, 80%, 85%, 90%, 95% or 99% identity with SEQ ID Nos: 25-27.

In a preferred embodiment, the short fragment conjugated to the surface of AuNP is SH-COC-5335-SF-1X according to SEQ ID No. 23 or a sequence sharing at least 50%, 55%, 60%, 65%, 70%, 75%, 80%, 85%, 90%, 95% or 99% identity with SEQ ID No: 23.

In specific embodiments, the CBSA selective for cocaine is COC-CBSA-5325, COC-CBSA-5335, COC-CBSA-5435, COC-CBSA-5445, or a sequence sharing at least 50%, 55%, 60%, 65%, 70%, 75%, 80%, 85%, 90%, 95% or 99% identity with COC-CBSA-5325, COC-CBSA-5335, COC-CBSA-5435 or COC-CBSA-5445.

In one embodiment, this assay enables detection of cocaine at low micromolar concentration within 15 minutes in 10% saliva.

In one embodiment, the CBSA-based EATR-amplified colorimetric assay is target-specific. In other embodiment, the CBSA-based EATR-amplified colorimetric assay can be used to distinguish cocaine from other common cutting agents observed in street samples such as lidocaine, caffeine, levamisole, and benzocaine. As a result, the EATR colorimetric assay can be used for the specific and sensitive naked-eye detection of cocaine in seized samples.

In one embodiment, the subject invention provides a method for detecting small molecules that are biomarkers for diagnosis of diseases and conditions, or monitoring therapeutic response to specific treatments. In specific embodiments, the condition can be, for example, cancer, an injury, an inflammatory disease or a neurodegenerative disease.

In one embodiment, the aptamer engineering methods, detection assays, and aptamer products according to the subject invention will accelerate the development of sensitive and accurate sensors for detecting small-molecule targets in fields including environmental monitoring, food safety, law enforcement, medical diagnostics, and public health.

The subject invention encompasses the use of sequences having a degree of sequence identity or sequence similarity with the nucleic acid sequence(s) of the present invention. A similar sequence is taken to include a nucleotide sequence which may be at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the subject sequence. Typically, the similar sequences will comprise the same or similar secondary structure as the subject nucleic acid aptamer. In one embodiment, a similar sequence is taken to include a nucleotide sequence which has one or several additions, deletions, substitutions and/or chemical modifications compared with the subject sequence.

EXAMPLES

Materials and Methods

All DNA strands used in this work were synthesized by Integrated DNA Technologies and purified with high performance liquid chromatography. DNA was dissolved in PCR grade water and DNA concentrations were measured with a NanoDrop 2000 (Thermo Scientific). The sequences of the oligonucleotide strands are listed below in Table 1. Tris(hydroxymethyl)aminomethane (Tris), hydrochloric acid, sodium chloride, magnesium chloride, bovine serine albumin (BSA), 1,4-dithiothreitol (DTT), gold (III) chloride trihydrate, cocaine hydrochloride, and DIS were purchased from Sigma-Aldrich. Exo III was purchased from New England Biolabs. OliGreen and SYBR gold were purchased from Thermo Fisher Scientific. Urine samples used in this work were collected from healthy and consenting adult donors.

TABLE 1

The sequences of the oligonucleotide strands

| SEQ ID No. | Sequence ID | Sequence (5' - 3') |
| --- | --- | --- |
| SEQ ID No: 1 | DISS.1-AT | CTCGGGACGTGGATTTTCCGCATACGAAGTTGTCCCGAG |
| SEQ ID No: 2 | DIS-4536-LF | GTCCGCATACGAAGTTGTCTTCCGCATACGAAGTTGTCCAAAAA |
| SEQ ID No: 3 | FQ-DIS-4536-SF | /5IAbRQ/GGACGTGGA/iSpC3/GACGTGGAC/iCy5/AAAAA |
| SEQ ID No: 4 | DIS-36-LF | GTCCGCATACGAAGTTGTCAAAAA |
| SEQ ID No: 5 | FQ-DIS-36-SF | /5IAbRQ/GACGTGGAC/iCy5/AAAAA |
| SEQ ID No: 6 | DIS-536-LF | GTCCGCATACGAAGTTGTCTTCCGCAAAAA |
| SEQ ID No: 7 | FQ-DIS-536-SF | /5IAbRQ/GTGGA/iSpC3/GACGTGGAC/iCy5/AAAAA |
| SEQ ID No: 8 | DIS-4536-SF | GGACGTGGA/iSpC3/GACGTGGACAAAAA |
| SEQ ID No: 9 | COC-5325-LF | CTCCTTCAACGAAGTGGGTTCCTTCAACGAAGTGGGTCTC |
| SEQ ID No: 10 | COC-5325-SF | GAGACAAGG/iSpC3/ACAAGGAG |

TABLE 1-continued

The sequences of the oligonucleotide strands

| SEQ ID No. | Sequence ID | Sequence (5' - 3') |
|---|---|---|
| SEQ ID No: 11 | COC-5335-LF | CTCCTTCAACGAAGTGGGTCTCCTTCAACGA AGTGGGTCTC |
| SEQ ID No: 12 | COC-5335-SF | GAGACAAGG/iSpC3/GACAAGGAG |
| SEQ ID No: 13 | COC-5435-LF | CTCCTTCAACGAAGTGGGTCTTCCTTCAACG AAGTGGGTCTC |
| SEQ ID No: 14 | COC-5435-SF | GAGACAAGGA/iSpC3/GACAAGGAG |
| SEQ ID No: 15 | COC-5445-LF | CTCCTTCAACGAAGTGGGTTCTTCCTTCAAC GAAGTGGGTCTC |
| SEQ ID No: 16 | COC-5445-SF | GAGACAAGGA/iSpC3/GAACAAGGAG |
| SEQ ID No: 17 | COC-5325-LF-P | CTCCTTCAACGAAGTGGGTTCCTTCAACGA AGTGGGTCTCTTTTT |
| SEQ ID No: 18 | COC-5325-LF-B | CTCCTTCAACGAAGTGGGTTCCTTCAACGA AGTGGGTCTCT/3InvdT/ |
| SEQ ID No: 19 | COC-5325-SF-P | GAGACAAGG/iSpC3/ACAAGGAGTTTTT |
| SEQ ID No: 20 | COC-5325-SF-B | GAGACAAGG/iSpC3/ACAAGGAGT/3InvdT/ |
| SEQ ID No: 21 | FQ-COC-5325-SF-B | /5IAbRQ/GAGACAAGG/iSpC3/ACAAGGAGT/iCy5/T/3InvdT/ |
| SEQ ID No: 22 | COC-5325-LF-P-18 | CTCCTTCAACGAAGTGGGTTCCTTCAACGA AGTGGGTCTCTTTTTTTTTTTTTTTTT |
| SEQ ID No: 23 | SH-COC-5335-SF-1X | HS-(CH$_2$)$_6$-TTTTTTGAGACAAGG/iSpC3/GACAAGGAG |
| SEQ ID No: 24 | COC-5335-LF-3'A | CTCCTTCAACGAAGTGGGTCTCCTTCAACGA AGTGGGTCTCAAAAA |
| SEQ ID No: 25 | COC-5335-SF-5'A | AAAAAGAGACAAGG/iSpC3/GACAAGGAG |
| SEQ ID No: 26 | COC-5335-SF-3'A | GAGACAAGG/iSpC3/GACAAGGAGAAAAA |
| SEQ ID No: 27 | COC-5335-SF-T | AAAAAGAGACAAGGTGACAAGGAG |
| SEQ ID No: 28 | SH-COC-5335-SF-2X | HS-(CH$_2$)$_6$-/TTTTTTGAGACAAGG/iSpC3/GACAAGGAGT TTTTTGAGACAAGG/iSpC3/GACAAGGAG | a /iSpC3/ represents internal C3 spacer modification
b /5IAbRQ/ represents Iowa Black RQ quencher modification
c. /iCy5/ represents Cy5 fluorophore modification
d. /3InvdT/ represents a 3' inverted deoxythymidine.

Isothermal Titration Calorimetry (ITC)

ITC experiments were performed with a MicroCal ITC200 (Malvern). 200 μM DIS was titrated into 10 μM DISS.1-AT, with both diluted in DIS binding buffer (10 mM Tris-HCl, 0.5 mM MgCl$_2$, pH 7.4). The experiment consisted of 19 successive 2 μL injections after an initial 0.4 μL purge injection with spacing of 180 seconds at 23° C. The injection heat was analyzed with the MicroCal analysis kit integrated into Origin 7 software, and the titration curve was fitted with a single-site binding model.

Determination of Binding Affinity of DIS-CBSA-4536, DIS-SA-536 and DIS-SA-36

The binding affinities of the split aptamers were determined using a previously reported fluorescence assay with some modifications. 1 μL of 100 μM DIS long fragment (DIS-4536-LF, DIS-536-LF or DIS-36-LF), 1 μL of 100 μM respective fluorophore/quencher-modified DIS short fragment (FQ-DIS-4536-SF, FQ-DIS-536-SF or FQ-DIS-36-SF), and 93 μL of DIS binding buffer were mixed with 5 μL of solution containing various concentrations of DIS. 80 μL of each sample was then transferred into wells of a 96-well plate. After a 30-minute incubation at room temperature, the fluorescence was measured using a TECAN M1000 Pro ($\lambda_{ex/en}$=648/668 nm). Each sample was analyzed in triplicate, and the means and standard deviations were plotted. The data were fitted with the Hill equation using OriginLab 9 to calculate Hill coefficient ($n_H$) and $K_{1/2}$ (DIS concentration producing half occupancy) of each split aptamer.

Exo III Digestion and Gel Electrophoresis Analysis

All digestion experiments were performed as followed unless specified otherwise. 1 μL each of 50 μM short and long CBSA fragments were added into 43 μL of reaction buffer to yield final DIS and cocaine concentrations of 250 μM and 500 μM, respectively. The buffer composition varied for each aptamer/target mixture, with final concentrations for each reaction as follows: DIS (10 mM Tris-HCl, 0.5 mM MgCl$_2$, 0.1 mg/mL BSA, pH 7.4) and cocaine (10 mM Tris-HCl, 0.1 mM MgCl$_2$, 0.1 mg/mL BSA, pH 7.4). After incubation at 23° C. for 30 minutes, 5 µL of 0.01 U/µL Exo III was added. After 5, 10, 15, 30, and 60 minutes of digestion, 5 µL of each sample was collected and immediately mixed with 10 µL of loading buffer (71.25% formamide, 10% glycerol, 0.125% SDS, 25 mM EDTA, and 0.15% (w/v) xylene cyanol) to inactivate Exo III. Control samples were prepared similarly, but with 5 µL reaction buffer instead of Exo III. The digestion products were characterized via denaturing polyacrylamide gel electrophoresis (PAGE), with 3 µL of each sample loaded into each well. Separation was carried out at 20 V/cm for 3 hours in 0.5×TBE running buffer. The gel was stained with 1×SYBR Gold for 25 minutes and imaged using a ChemiDoc MP imaging system (Bio-Rad). The percent of digestion was calculated based on band intensity relative to the control sample.

CBSA-Based, EATR-Amplified Fluorescence Assay for Detection of DIS

2 µL of 100 µM DIS-4536-LF or DIS-536-LF, 1 µL of 100 µM FQ-DIS-4536-SF or FQ-DIS-536-SF, and 92 µL of DIS binding buffer (10 mM Tris-HCl, 0.5 mM MgCl$_2$, pH 7.4) or 50% urine diluted with the binding buffer were mixed with 5 µL of solution containing various concentrations of DIS in the wells of a 96-well plate. The fluorescence of each sample was first measured ($\lambda_{ex/en}$=648/668 nm) after a 30-minute incubation at room temperature. Then, 5 µL of 0.2 U/µL Exo III was added into each well to initiate EATR. After a 30-minute digestion at room temperature, the fluorescence of each sample was measured again. The signal gain was calculated by (F–F$_0$)/F$_0$×100%, where F$_0$ is the fluorescence of the split aptamer mixtures without DIS and F is the fluorescence of the split aptamer mixtures with different concentrations of DIS. Error bars were calculated from standard deviation of signal gains from three individual measurements at each DIS concentration.

Synthesis of Gold Nanoparticles (AuNPs) Modified with Cocaine-Binding CBSA Short Fragment The modification of the thiolated short fragment (SH-COC-5335-SF-1X or SH-COC-5335-SF-2X) onto 13-nm AuNPs was performed using a previously published protocol, at a 300:1 molar ratio of thiolated short fragment:AuNP. The modified AuNPs were then treated with DTT to regulate surface coverage. Specifically, 50 µL of 5 nM modified AuNPs were mixed with 20 µL of solution containing different concentrations of DTT in 10 mM Tris-HCl (pH 7.4). After a 30-minute incubation, the solution was centrifuged at 28,000× ref for 10 minutes. The supernatant was discarded to remove the excess DTT and displaced DNA strands, and the precipitated AuNPs were resuspended in 10 mM Tris-HCl (pH 7.4). This step was repeated twice. Finally, the modified AuNPs were resuspended in 5 µL of the same buffer to obtain a particle concentration of 50 nM.

Quantitation of the Surface Coverage of CBSA Short Fragments on AuNPs Via DTT Displacement Surface coverage of the SH-COC-5335-SF-1X- or SH-COC-5335-SF-2X-modified AuNPs were measured using a standard DTT displacement assay. The AuNPs were diluted to a final volume of 55 µL in Tris buffer (10 mM Tris-HCl, pH 7.4). 50 µL of AuNP solution was loaded into a well of a 384-well plate and the absorbance was measured using a TECAN M1000 Pro. The concentration of AuNPs was calculated using Beer's law ($\epsilon$=2.7×10$^8$ mol$^{-1}$·cm$^{-1}$). 50 µL of the modified AuNP solution was collected and mixed with 50 µL of 1.0 M DTT solution. After an overnight incubation at room temperature, the solution was centrifuged at 25,000× ref for 10 minutes to remove the AuNP precipitate. 20 µL of the supernatant was then mixed with 80 µL of 0.625× OliGreen solution to obtain a 0.5× Oligreen concentration. 100 µL of supernatant-Oligreen mixture was loaded into a well of a 384-well microplate and fluorescence was measured using a TECAN M1000 Pro ($\lambda_{ex/em}$=500/525 nm). DTT-displaced oligonucleotides were quantified using an established calibration curve derived from CBSA short fragments that had been subjected to the same DTT treatment.

CBSA-Based, Colorimetric EATR Assay for Detection of Cocaine 2.5 µL of SH-COC-5335-SF-1X- or SH-COC-5335-SF-2X-modified AuNPs (50 nM), 1 µL of 2.5 µM long fragment (COC-5335-LF), 2 µL of a solution with different cocaine concentrations or different cutting agents with a final concentration of 50 and 15.5 µL reaction buffer (final concentrations: 10 mM Tris-HCl, 100 mM NaCl, 0.75 mM MgCl$_2$, 0.1 mg/mL BSA, pH 7.4) were mixed in wells of a 384-well plate. After 30 minutes, 4 µL of 1.25 U/µL Exo III was added into each well. Absorbance spectra from 400-800 nm were recorded every 5 minutes, with pictures taken by a Nikon D800 after 20 minutes of Exo III digestion.

Example 1—Engineering of DIS-Binding CBSA

Figures 2A, 2B, 2C, 2D:
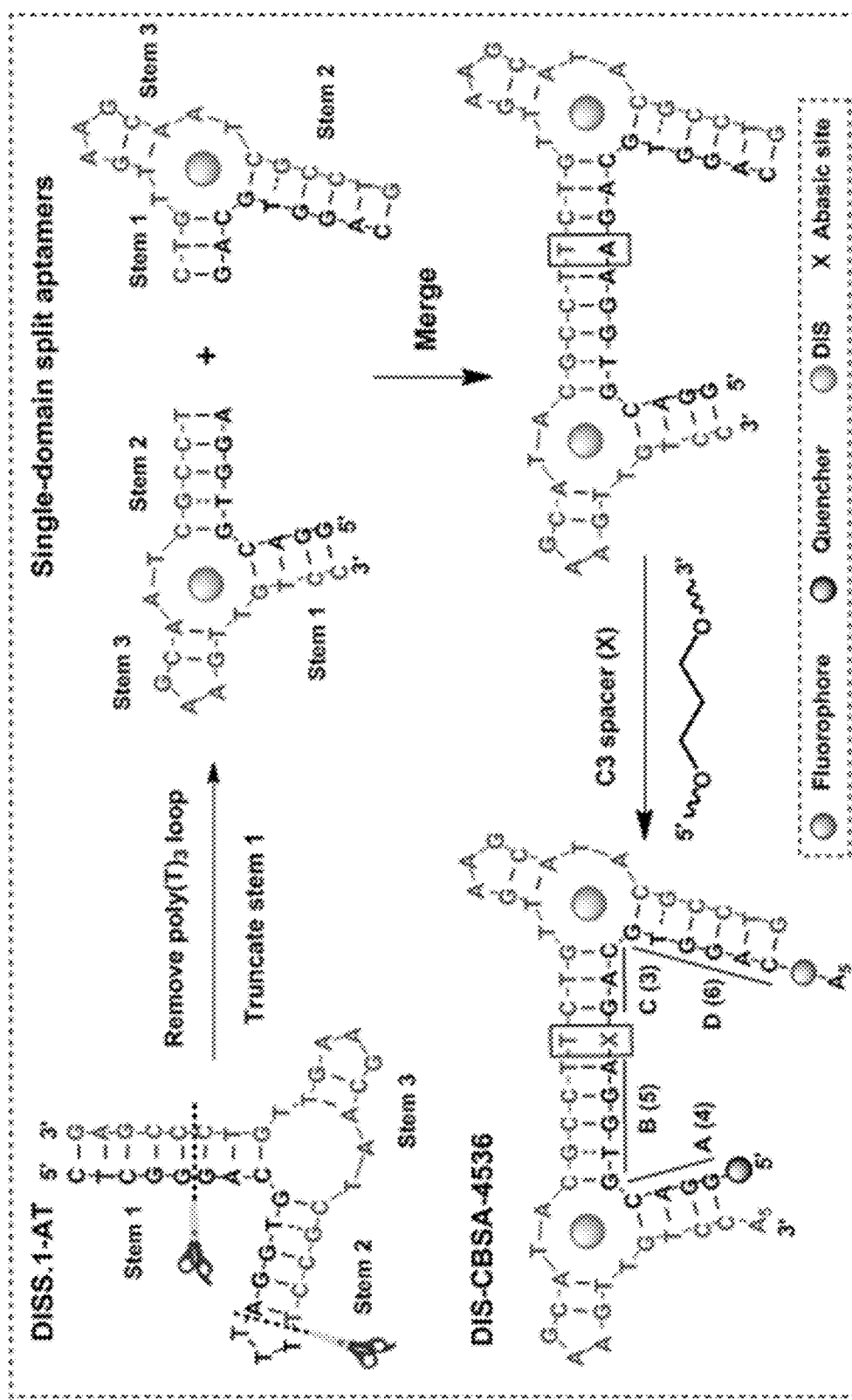
FIGS. 2A-2D show a design of a DIS-binding CBSA. (2A) DISS.1-AT (SEQ ID No: 1) was truncated at Stem 1 and Stem 2 to generate the parent split aptamers. (2B) Two sets of parent split aptamers were (2C) merged and modified to incorporate (2D) a C3 spacer abasic site (denoted by X) that resides opposite a thymine nucleotide when the CBSA duplex is assembled. A fluorophore (Cy5) and a quencher (Iowa Black RQ) were respectively modified at the 3' and 5' terminus of the short CBSA fragment. A poly $(A)_5$ overhang was added on the 3' termini of the long and short fragments to generate DIS-4536-LF (SEQ ID No: 2) and FQ-DIS-4536-SF (SEQ ID No: 3), respectively, to prevent non-specific Exo III digestion.

Stojanovic and colleagues recently isolated aptamers for various steroids, including DIS, using a library-immobilized SELEX approach. DIS is one of the most abundant steroid hormones in urine. The concentration of DIS in healthy adults typically ranges from 1-20 µM, but can climb to the sub-millimolar range in patients with adrenal tumors. The isolated DIS-binding aptamer (DISS.1-AT) demonstrated a K$_D$ of 0.44 µM (FIG. 1). DISS.1-AT was used as a starting point for the CBSA engineering strategy described previously. First, parent split aptamers were generated by removing the poly (T)$_3$ loop region from DISS.1-AT (SEQ ID No: 1) and reducing the number of base pairs in stem 1 (FIG. 2A). Then a DIS-binding CBSA was fabricated by fusing two sets of these parent split aptamers as shown in FIG. 2B. The engineered CBSA consists of a short fragment and a long fragment. To facilitate EATR, the adenosine at position 9 from the 5' end of the short fragment was replaced with a C3 spacer abasic site (labeled as X in FIG. 2C). In the presence of DIS, these two fragments assemble to form DIS-CBSA-4536 complex (FIG. 2D), where the C3 spacer abasic site is opposite a thymine within the long fragment. Exo III can cleave the short fragment at this duplexed abasic site using its apurinic endonuclease activity, releasing the intact long fragment and DIS molecules.

Example 2—Design of a CBSA-Based EATR-Amplified Fluorescence Assay

To confirm binding cooperativity of DIS-CBSA-4536, the short fragment was modified with a Cy5 fluorophore and an Iowa Black RQ quencher at the 3' and 5' terminus, respectively (FQ-DIS-4536-SF) (SEQ ID No: 3) (FIG. 2D).

In the absence of the target, both FQ-DIS-4536-SF and the corresponding long fragment (DIS-4536-LF) remain separate, and the fluorophore is quenched due to its close proximity with the quencher (FIG. 3A). Upon the addition of DIS, the two fragments assemble to form a rigid CBSA-target complex, separating the fluorophore from the quencher and resulting in elevated fluorescence (FIG. 3B).

By titrating various DIS concentrations, a Hill coefficient (n$_H$) of 1.6 was determined for DIS-CBSA-4536 (FIG. 4A), indicating considerable positive cooperativity. This implies that a transition of CBSA assembly from 10% to 90% requires only a 16-fold increase in target concentration, compared to its parent split aptamers which require an 81-fold increase. NUPACK analysis of the DIS-binding CBSA sequences demonstrated that both fragments are predominantly unassembled (99%) in the absence of target under the experimental conditions but DIS-4536-SF exists primarily as a duplexed structure (FIG. 5A). Therefore, binding of the first target to DIS-CBSA-4536 should open up the duplex of DIS-4536-SF, facilitating binding of a second DIS molecule to the CBSA. This results in a high level of cooperativity. A $K_{1/2}$ of 491 µM was obtained, where $K_{1/2}$ represents the DIS concentration at which half of the binding domains are occupied (FIG. 4A).

To demonstrate the highly sensitive target-induced assembly of the CBSA, two sets of DIS-binding split aptamers were designed with a single binding domain. Specifically, Stem 1 of the DIS-binding parent split aptamer (termed DIS-SA-36) (FIG. 2B, right and FIG. 4B) was extended by one abasic site and five base pairs to form a split aptamer with a longer stem (termed DIS-SA-536) (FIG. 4C). The long fragments were unmodified while the short fragments were modified with a Cy5 fluorophore and an Iowa Black RQ quencher at the 3' and 5' terminus, respectively.

Binding experiments were performed with these two split aptamers along with the CBSA. DIS-CBSA-4536 demonstrated no background assembly in the absence of the target, and progressive target-induced assembly with increasing concentrations of DIS. DIS-SA-536 also showed target-induced assembly with a moderately higher target affinity, but had high background assembly in the absence of DIS (FIG. 4A). No cooperativity was observed ($n_H$=1.05) with this single-binding pocket split aptamer. The parent split aptamer, DIS-SA-36, was unable to assemble regardless of the presence or absence of target due to its thermal instability (FIG. 4A).

The affinity of DIS-CBSA-4536 was too low for direct detection of DIS at physiological relevant concentrations. Nevertheless, the highly target-responsive feature of the CBSA enables the demonstration of its compatibility with EATR-mediated signal amplification. Exo III was selected for this reaction because of its potent apurinic endonuclease activity, along with the fact that this enzyme is highly active at room temperature in a sequence-insensitive manner. When the CBSA-DIS complex assembles in the presence of DIS, Exo III is able to recognize the duplexed structure and specifically cleaves it at the abasic site (FIG. 3C). This cleavage results in disassembly of the CBSA-target complex, releasing the long fragment, DIS molecules, and the fluorophore, which now fluoresces due to its separation from the quencher. The released long fragment and target are then free to assemble with another FQ-DIS-4536-SF (FIG. 3D), starting the cycle anew.

The end result is that a very small amount of target can be recycled for multiple rounds of assembly and cleavage, generating a substantially amplified fluorescence signal (FIG. 3E).

Example 3—Exo III Efficiently Mediates EATR of DIS-CBSA-4536 in Solution

In order to prevent nonspecific digestion of the CBSA, a poly $(A)_5$ overhang was added at the 3' terminus of both the short and long fragments. A time-course of digestion with Exo III using DIS-CBSA-4536 was performed in the presence or absence of DIS. The digestion products were collected after 5, 10, 15, 30, 60, and 120 minutes and analyzed by polyacrylamide gel electrophoresis (PAGE) (FIG. 6A). The concentration of retained DIS-4536-SF was calculated relative to a control sample that was untreated with Exo III.

Exo III cleavage of DIS-4536-SF was rapid and specific, with 59% cleavage in the presence of 500 µM DIS after 30 minutes. In contrast, only 9% of DIS-4536-SF was cleaved in the absence of the target (FIG. 6B). After 120 minutes, DIS-4536-SF was almost completely cleaved (95%) in the DIS sample, compared to only 15% cleavage in the absence of the target (FIG. 6B).

These results confirmed that the apurunic endonuclease activity of Exo III could specifically cleave the CBSA even when it is bound to the DIS target. Notably, moderate non-specific digestion of DIS-4536-LF by Exo III was observed, resulting in partial removal of its poly$(A)_5$ protection (FIG. 6A). The total concentration of DIS-4536-LF and its products, calculated from the intensity of all bands larger than 39 nt, remained constant after a 120-minute digestion (FIG. 6C). Since all digested products contained the intact recognition segments of the CBSA, EATR efficiency was not affected.

Recycling of target and long fragment were demonstrated by performing an Exo III cleavage reaction with 1 µM DIS-4536-LF and 4 µM DIS-4536-SF in the presence of 500 µM DIS. PAGE analysis confirmed that Exo III achieved efficient and specific cleavage of the short fragment, with 99% of DIS-4536-SF cleaved after 240 minutes (FIG. 7A). In contrast, only 11% of DIS-4536-SF was cleaved in the absence of DIS (FIG. 7B). Less than 15% of DIS-4536-LF was digested regardless of the presence or absence of target (FIG. 7C).

Based on the fact that the short fragment was almost completely cleaved despite being present at a concentration greatly exceeding that of the long fragment, it is clear that Exo III-mediated recycling of the long fragment and target was taking place.

Figure 8A:
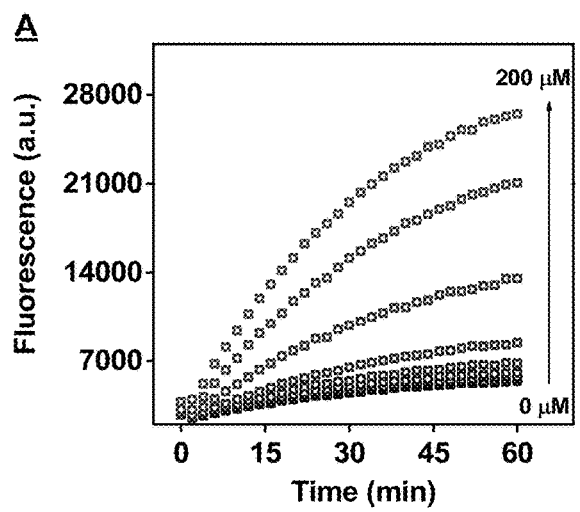
FIGS. 8A-8B show CBSA-based EATR-amplified fluorescence assay for sensitive detection of DIS using DIS-4536-LF and FQ-DIS-4536-SF. (8A) Fluorescence time-course measurements after adding 0.01 U/μL of Exo III to DIS-CBSA-4536 in the presence of different concentrations of DIS (0, 0.5, 1, 2, 5, 10, 20, 50, 100 and 200 μM). (8B) Calibration curves before (black) and 30 minutes after (red) EATR signal amplification. The inset shows the calibration curve at low DIS concentrations. The signal gain was calculated from the fluorescence intensity of the samples. Error bars represent the standard deviation of three measurements. Limit of detection is determined using the lowest non-zero calibrator concentration.
Figure 8B:
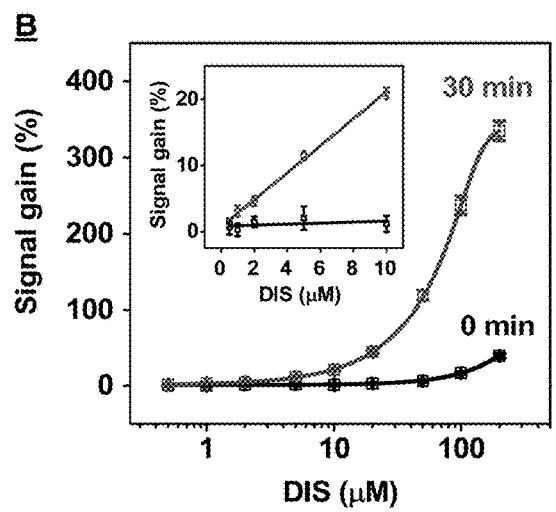

Example 4—Sensitive DIS Detection in Biofluid Samples Using CBSA-Based EATR-Amplified Fluorescence Assay Having demonstrated the feasibility of the CBSA-based EATR-amplified approach, the fluorescence assay described in FIGS. 3A-3E was performed to detect DIS. When 1 µM FQ-DIS-4536-SF was incubated with 2 µM DIS-4536-LF and different concentrations of DIS for 30 minutes, no significant DIS-induced fluorescence change was observed even with 100 µM DIS (FIGS. 8A and 8B, 0 min), as target binding of the CBSA was too weak to efficiently assemble the CBSA-target complex. However, after adding 0.01 U/µL of Exo III, a steady and concentration-dependent increase in fluorescence occurred (FIG. 8A). The initial rate at which fluorescence increased was proportional to the DIS concentration, and concentrations as low as 1 µM could be detected after 30 minutes of cleavage (FIG. 8B, inset). The fluorescence of the samples without DIS also increased to some extent due to the nonspecific digestion of FQ-DIS-4536-SF (FIG. 8A, 0 µM).

These results demonstrate that the sensitivity of the CBSA binding assay was enhanced 100-fold by implementing EATR, producing a measurable limit of detection that is more than 500-fold lower than the $K_{1/2}$ of the CBSA.

Figure 9A:
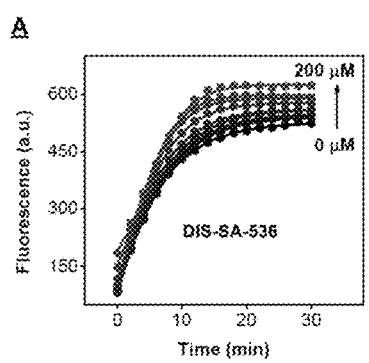
FIGS. 9A-9C show demonstration of EATR-amplified signal in a fluorophore-quencher assay. Time course digestion of (9A) DIS-SA-536 and (9B) DIS-CBSA-4536 with 0, 0.5, 1, 2, 5, 10, 20, 50, 100, and 200 μM DIS. (9C) Calibration curves of the fluorophore-quencher assay obtained with both split aptamers before and after 30 minutes of EATR signal amplification.
Figure 9B:
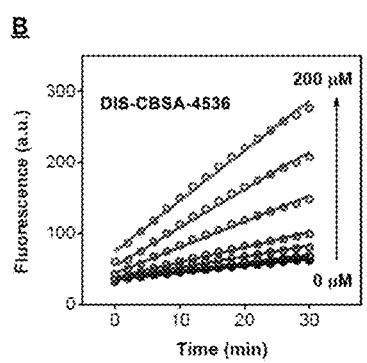
Figure 9C:
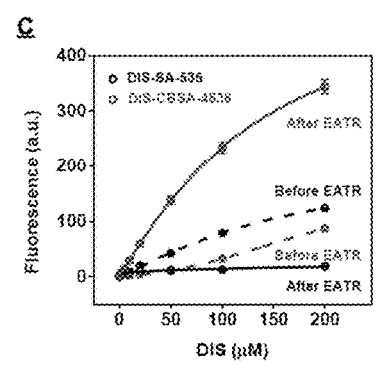

As a control experiment, the EATR-amplified fluorescence assay was also performed using DIS-SA-536. Although DIS-SA-536 underwent target-induced assembly and was efficiently cleaved by Exo III, no target-induced signal amplification occurred after a 30-minute digestion because of the high levels of DIS-independent background assembly (FIGS. 9A and 9C). In contrast, DIS-CBSA-4536 exhibited clear target-induced signal amplification (FIGS. 9B and 9C), with rapid assembly occurring at very low concentrations of target and minimal background assembly in the absence of target.

Importantly, the assay performed equally well in urine samples. Different concentrations of DIS were spiked into 50% diluted urine and tested with the CBSA-based EATR-amplified fluorescence assay. After a 30-minute enzyme digestion, a calibration curve was obtained with a linear range from 0 to 100 µM (FIG. 10A), which covers the urinary DIS concentration range in normal adults (1-50 µM). In addition, concentrations as low as 1 µM DIS spiked in 50% urine could be distinguished from the background signal (FIG. 10B). The results clearly demonstrated the robustness and sensitivity of the CBSA-based EATR fluorescence assay even in complex samples.

Example 5—Design of a Cocaine-Binding CBSA

To demonstrate the cooperative target binding of a split cocaine-binding aptamer, a previously reported 38-nucleotide cocaine-binding aptamer (38-GC) (Roncancio et al. *Anal. Chem.*, 2014, 86 (22), pp 11100-11106) was split (FIG. 11A) into two fragments. It is known that 38-GC is a TWJ-structured aptamer, containing three stems and two loops. Compared to the stem-2 AAA loop, the stem-3 GAA loop contributes more to cocaine binding. Therefore, the stem-3 loop was kept intact and the stem-2 loop was removed to form a split aptamer containing a single target-binding domain termed single binding split aptamer (SSA).

To achieve cooperative target binding, several base-pairs in stem 1 and stem 2 were further truncated in each set of SSA (FIG. 11B) and these two sets of truncated SSAs were merged to create a CBSA termed COC-CBSA-5325, which consists of a long fragment (LF) and a short fragment (SF) (FIG. 11C). An abasic C3 spacer was incorporated into the short fragment with a thymine incorporated opposite to the spacer in the long fragment (FIG. 11D).

In the absence of target, the short and long fragments are separated. However, in the presence of target, these two fragments assemble via cooperative target binding to form a CBSA-target complex that contains two target-binding domains.

Figures 12A, 12B, 12C:
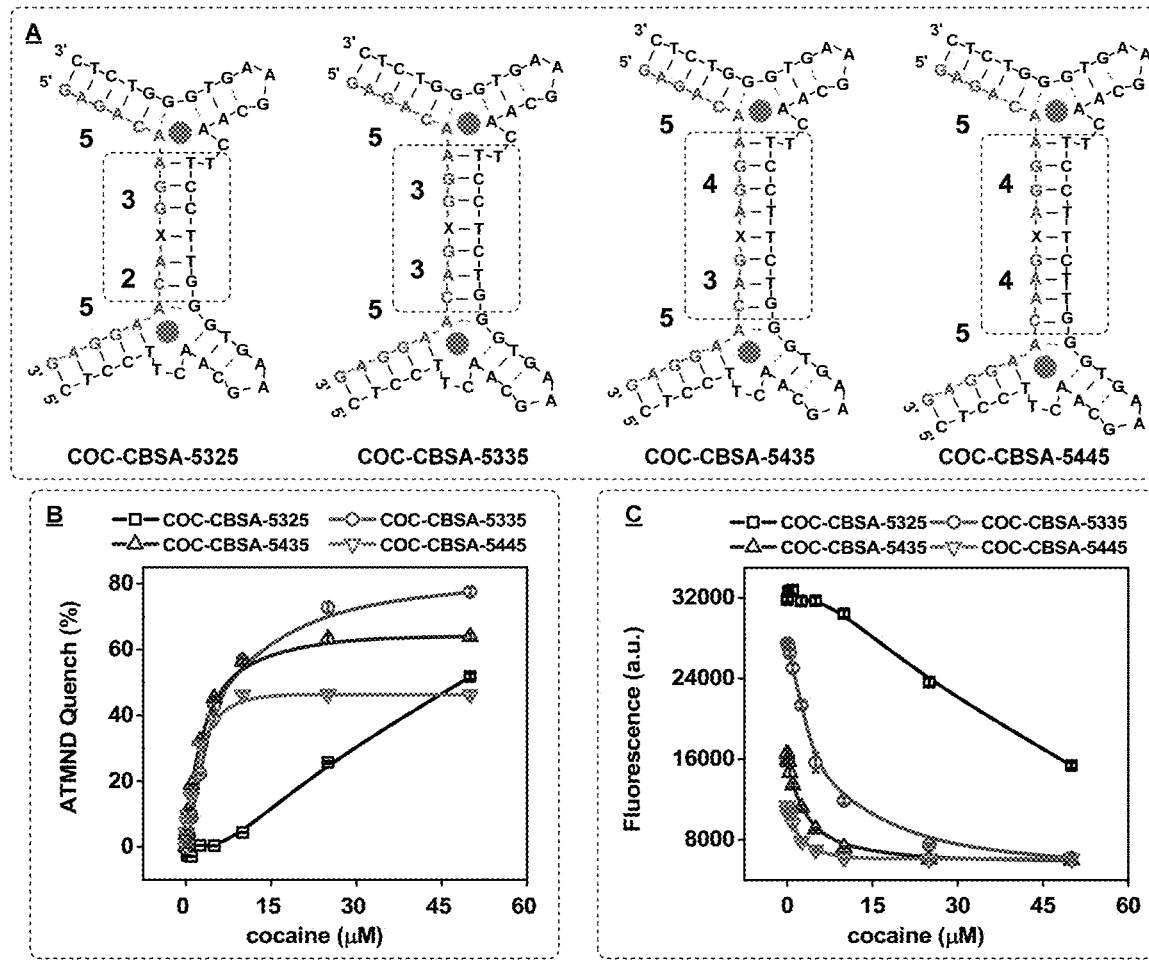
FIGS. 12A-12C show the stem length effects on cocaine-induced CBSA assembly. (12A) Sequences of COC-CBSA-5325, COC-CBSA-5335 (which consists of COC-5335-LF (SEQ ID No: 11) and COC-5335-SF (SEQ ID No: 12), COC-CBSA-5435 (which consists of COC-5435-LF (SEQ ID No: 13) and COC-5435-SF (SEQ ID No: 14), and COC-CBSA-5445 (which consists of COC-5445-LF (SEQ ID No: 15) and COC-5445-SF (SEQ ID No: 16). (12B) 2-amino-5,6,7-trimethyl-1,8-naphthyridine (ATMND) (200 nM) fluorescence upon addition of 1 μM COC-CBSA-5325, COC-CBSA-5335, COC-CBSA-5435 or COC-CBSA-5445 at various cocaine concentrations (0-50 μM). (12C) ATMND-reported calibration curve for these CBSA variants at varying cocaine concentrations. Percent of fluorescence quenching was calculated by $(F_0-F)/F_0 \times 100\%$, where $F_0$ and F are the fluorescence of the ATMND-CBSA in the absence and presence of cocaine, respectively.

Other cocaine binding CBSAs were created by increasing the total number of base-pairs between the two binding domains of COC-CBSA-5325. For example, COC-CBSA-5335, COC-CBSA-5435 and COC-CBSA-5445 were generated by adding an additional one, two, or three base-pairs between the two binding domains (FIG. 12A). The extent of their target-induced CBSA assembly at different cocaine concentrations (0-50 µM) was examined using an ATMND-binding assay.

ATMND is a fluorescent dye that can insert itself into duplexed abasic sites. When ATMND is free in solution, it fluoresces, but its fluorescence becomes quenched when it binds to duplexed abasic sites of the CBSA-cocaine complex in the presence of cocaine (FIGS. 12B and 12C). The results demonstrate that the number of additional base-pairs affects both binding affinity and target-induced assembly. In the absence of cocaine, the quenching of ATMND fluorescence increased as the number of base-pairs between the two CBSA binding domains increased from 5- to 8-bp (FIG. 12B). A strong correlation between ATMND quenching from CBSA assembly and cocaine concentration in the range of 0 to 50 µM was demonstrated in FIG. 12C.

Figures 13A, 13B, 13C, 13D, 13E:
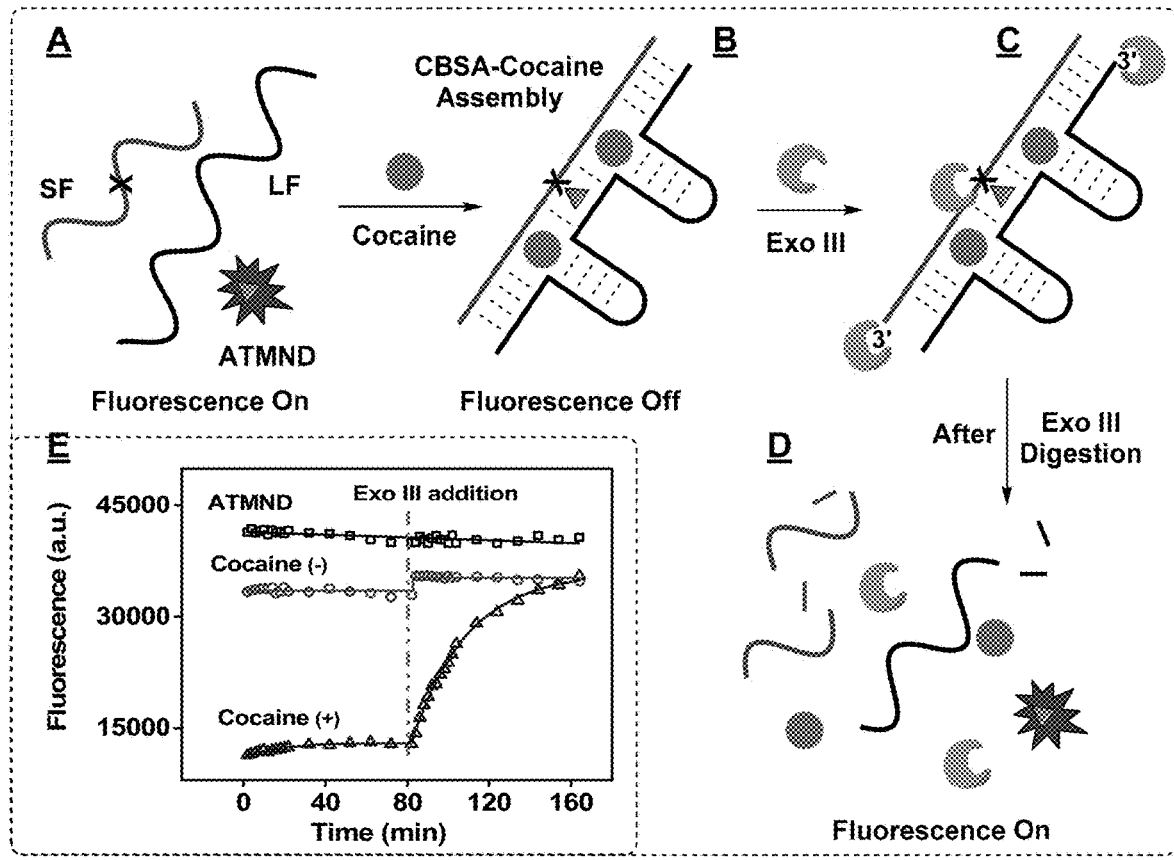
FIGS. 13A-13E show the use of ATMND to determine target-induced assembly of COC-CBSA-5325 and assess Exo III digestion of the CBSA-cocaine complex. (13A-13D) The working principle of the ATMND assay. (13A) The long fragment (COC-5325-LF) and short fragment (COC-5325-SF) remain separate without cocaine, and ATMND is free in solution, emitting fluorescence. (13B) The two fragments assemble upon addition of cocaine, forming a CBSA-cocaine complex containing a duplexed abasic C3 spacer that binds ATMND, significantly quenching its fluorescence. (13C) Upon addition of Exo III, the enzyme cleaves the abasic site of the short fragment, releasing the target, long fragment, and ATMND which results in an increase in fluorescence (13D). (13E) The time-course fluorescence change of ATMND upon addition of 0.1 U/μL Exo III in binding buffer with only 200 nM ATMND (black line) or binding buffer with 200 nM ATMND, 1 μM COC-5325-LF, and 1 μM COC-5325-SF in the absence (red line) and presence (blue line) of 250 μM cocaine.

Example 6—Assessment of Target-Induced CBSA Assembly and Exo III Digestion of the CBSA-Target Complex Using a Fluorescent Dye-Based Assay The target binding cooperativity of COC-CBSA-5325 and the Exo III digestion of the CBSA-cocaine complex was demonstrated using ATMND. When ATMND is free in solution, it fluoresces, but its fluorescence becomes quenched when it binds to duplexed abasic sites. In the absence of cocaine, the short and long fragments remain separate and ATMND fluoresces as it is free in solution (FIG. 13A). In the presence of cocaine, both fragments assemble to form the CBSA-cocaine complex containing a duplexed C3 spacer abasic site which ATMND then binds to, reducing its fluorescence significantly (FIG. 13B).

Upon the addition of Exo III, the enzyme recognizes and cleaves the duplexed abasic site, releasing the target, long fragment, and ATMND (FIG. 13C). Since the ATMND becomes freed into solution, it emits a strong fluorescence signal once again (FIG. 13D). In contrast, Exo III is not able to digest the single-stranded CBSA fragments in the absence of cocaine, therefore no change in fluorescence occurs.

To perform the ATMND assay, 1 µM each of both CBSA fragments (COC-5325-LF and COC-5325-SF) was mixed with 200 nM ATMND in binding buffer (10 mM Tris-HCl, 0.1 mM $MgCl_2$, pH 7.4) in the presence or absence of 250 µM cocaine. The change in the fluorescence of ATMND was used to determine the extent of CBSA assembly. After a 10-minute incubation at room temperature, 72% and 28% of ATMND was quenched with and without cocaine, respectively (FIG. 13E). This result shows that cocaine can rapidly assemble both the short and long fragments to form the CBSA-cocaine complex.

Upon addition of 0.1 U/µL Exo III, the fluorescence of ATMND in the cocaine-free sample did not change significantly. In contrast, the fluorescence of ATMND in the cocaine-containing sample gradually increased (FIG. 13E). This result indicates that Exo III can digest the assembled CBSA-cocaine complex to release cocaine, the long fragment, and ATMND.

Figure 14:
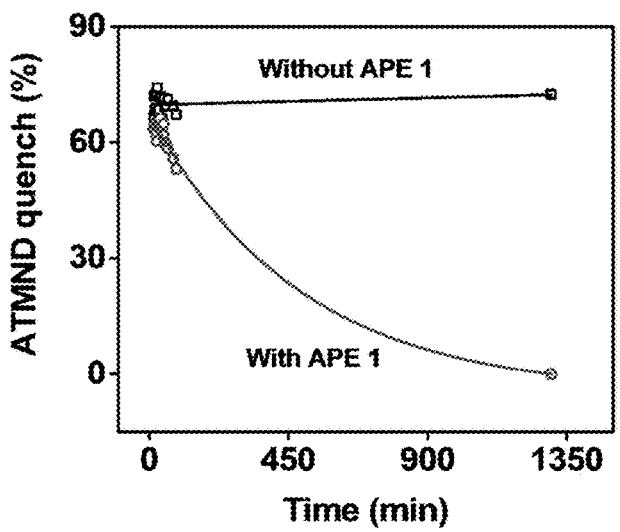
FIG. 14 shows the assessment of the digestion of the CBSA-cocaine complex by apurinic/apyrmidinic endonuclease 1 (APE1) using the ATMND assay. The fluorescence of ATMND was quenched upon the assembly of COC-CBSA-5325 in the presence of 250 μM of cocaine (black line). Upon addition of 0.3 U/μL APE1, quenching of ATMND fluorescence decreased due to freeing of the dye upon digestion of the CBSA-cocaine complex (red line). ATMND quench was calculated by $(F_0-F)/F_0 \times 100\%$, where $F_0$ is the fluorescence of the ATMND-CBSA mixture without cocaine and F is the fluorescence of the ATMND-CBSA mixture with 250 μM cocaine.

Another enzyme, AP endonuclease 1 (APE 1) (0.3 U/µL) was also used to perform the same experiment because this nuclease has apurinic endonuclease activity. However, a much lower efficiency of abasic site cleavage was observed using APE1 in the binding buffer. It took 20 hours for the cocaine-containing sample to achieve full ATMND fluorescence recovery (FIG. 14). Therefore, Exo III was hereon used for sensor development due to its high efficiency for enzyme digestion.

Example 7—Characterization of CBSA Digestion Products Using PAGE

PAGE was used to further identify and characterize the digestion of the CBSA-cocaine complex by Exo III. Specifically, 1 µM of both CBSA fragments were first incubated with or without 250 µM cocaine in binding buffer for 30 minutes at 23° C. Then, Exo III (0.01 U/µL) was added into each sample to initiate digestion.

Samples were collected after 30, 60, 120, 180, 240, and 300 minutes and mixed with a loading buffer containing EDTA, SDS, and formamide to stop enzyme digestion. The samples were loaded in the wells of a 15% polyacrylamide gel and separation was performed at 300 V for three hours. Afterwards, the gel was stained using SYBR Gold and band intensity was used to characterize the amount of digestion product generated.

The results show that 38% of COC-5325-SF is digested after 5 hours in the presence of 250 µM cocaine, while no significant digestion is observed without cocaine (FIG. 15). This indicates the successful Exo III digestion of CBSA-cocaine assembly. The 3' end of the COC-5325-LF was also digested regardless of the absence or presence of cocaine (FIG. 15). The digestion of the long fragment can be attributed to Exo III's 3' to 5' exonuclease activity.

Example 8—Modifications of the CBSA Long Fragment at its 3' Terminus

To prevent digestion of the long fragment, two modified versions were designed: one with a 3' poly $(T)_5$ extension (termed, COC-5325-LF-P and another with a single 3' inverted deoxythymidine (termed, COC-5325-LF-B). Each modified long fragment was used with COC-5325-SF to perform Exo III digestion in the presence and absence of 250 µM cocaine under the same conditions as described above.

The results show that the short fragment is completely digested for the CBSA mixture in the presence of cocaine while no short fragment digestion occurs in the absence of cocaine (FIG. 16A). A majority of COC-5325-LF-P is retained due to its poly $(T)_5$ protection, which is evidenced by COC-5325-LF-P's involvement in extensive target-induced CBSA assembly and digestion. On the other hand, digestion of COC-5325-SF in the mixture with COC-5325-LF-B was minimal, most likely due to the limited protection offered by the inverted deoxythymidine against exonuclease digestion of COC-5325-LF-B (FIG. 16A).

As a control experiment, Exo III digestion of a mixture of COC-5325-LF and COC-5325-SF was performed in the presence and absence of cocaine (FIG. 16A). No target-induced digestion was observed, which can be attributed to inability of the exonuclease-digested long fragment to participate in the assembly of the CBSA. Because COC-5325-LF-P demonstrated the greatest resistance to Exo III exonuclease digestion, this modified fragment was used for further experiments in Examples 9-11.

Example 9—Modification of the CBSA Short Fragment its 3'Terminus

Developing a fluorescence assay using the CBSA preferably requires modification of the short fragment with a fluorophore and a quencher at both of its termini. In the absence of target, the close proximity of the fluorophore and quencher results in minimal background fluorescence. However, a large background signal will be generated if Exo III removes the fluorophore or quencher through digestion of the 3' end of the short fragment. Thus, it is vital to protect the 3' end of the short fragment from enzyme digestion.

To do so, the 3' end of the short fragment was modified with an inverted deoxythymidine (COC-5325-SF-B) or a poly $(T)_5$ overhang (COC-5325-SF-P) and their resistance to Exo III digestion was tested with COC-5325-LF-P in the presence and absence of cocaine. As a result, only the inverted deoxythymidine modification was cleaved from COC-5325-SF-B without cocaine after 2 hours of digestion with 0.01 U/µL Exo III. However, cocaine was still able to assemble the cleaved COC-5325-SF-B with COC-5325-LF-P to successfully facilitate target-induced CBSA digestion (FIG. 16B).

Additionally, the poly $(T)_5$ protection of COC-5325-SF-P was partially digested both in the absence and presence of cocaine, generating a major product containing a poly $(T)_3$ overhang. This product was able to mediate target-induced CBSA assembly and digestion, but at a noticeably slower rate (FIG. 16B), possibly due to steric hindrance caused by the poly $(T)_5$ extension which prevented cleavage of the abasic site. COC-5325-SF in the mixture with COC-5325-LF-P was able to allow target-induced CBSA assembly and digestion at a similar rate as the COC-5325-LF-P and COC-5325-SF-B mixture. However, more non-specific digestion at its 3' end by Exo III was observed in the absence of cocaine (FIG. 16B). This 3' end digestion would result in a large background signal in a fluorophore-quencher assay, therefore, COC-5325-LF-P and COC-5325-SF-B were chosen for the development of an EATR assay.

Figures 17A, 17B:
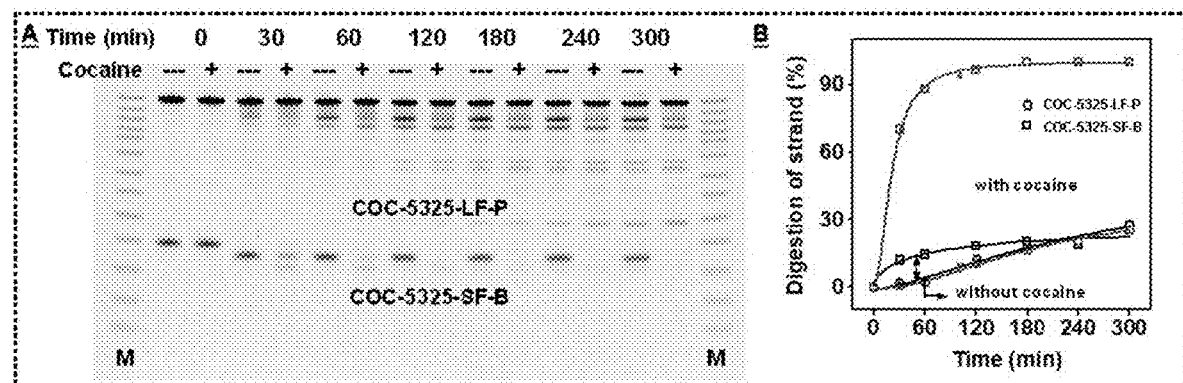
FIG. 17A-17B show the time-course digestion of the CBSA consisting of COC-5325-LF-P and COC-5325-SF-B characterized by 15% PAGE. (17A) PAGE analysis of digestion products from this CBSA. Reactions consisted of 1 μM of COC-5325-LF-P, 1 μM of COC-5325-SF-B, and 0.01 U/μL Exo III with or without 250 μM cocaine over a period of 300 minutes. (17B) Cleavage of COC-5325-LF-P and COC-5325-SF-B was quantified by $(Int_0-Int)/Int_0 \times 100\%$, where $Int_0$ and Int are the band intensities of either fragment before and after the addition of Exo III, respectively.

A time-course enzyme digestion was then performed using COC-5325-LF-P and COC-5325-SF-B, and the digestion products were characterized by 15% PAGE. 90% of the short fragment was digested in the presence of cocaine within one hour while only 20% of short fragment was digested without cocaine within 5 hours (FIG. 17). These results show that COC-5325-LF-P and COC-5325-SF-B can undergo efficient target-induced CBSA assembly and enzyme digestion only in the presence of target.

Figures 18A, 18B:
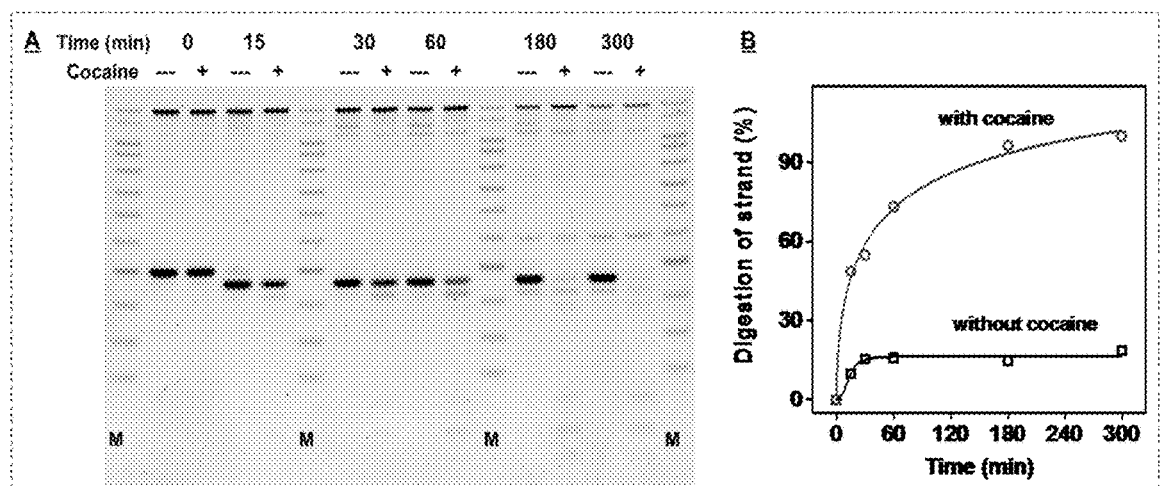
FIGS. 18A-18B show the time-course digestion of the CBSA consisting of COC-5325-LF-P and COC-5325-SF-B characterized by 15% PAGE. (18A) PAGE analysis of digestion products from this CBSA. Reactions consisted of 1 μM of COC-5325-LF-P, 8 μM of COC-5325-SF-B, and 0.1 U/μL Exo III with or without 250 μM cocaine. (18B) Cleavage of COC-5325-SF-B was quantified by $(Int_0-Int)/Int_0 \times 100\%$, where $Int_0$ and Int are the band intensities of either fragment before and after the addition of Exo III, respectively.

Example 10—Test Cooperative Target Binding Assisted Cocaine Recycling Using PAGE To demonstrate enzyme-assisted target recycling, digestion of COC-5325-LF-P and COC-5325-SF-B CBSA was performed using an 8-fold excess amount of short fragment relative to long fragment. Specifically, 1 µM of COC-5325-LF-P and 8 µM of COC-5325-SF-B was first incubated for 30 mins and then digested with 0.1 U/µL Exo III in the presence and absence of 250 µM cocaine. In the presence of cocaine, 95% of the short fragment was digested within 5 hours, indicating that at least 7 rounds of long fragment and cocaine recycling occurred (FIGS. 18A and 18B). In contrast, 15% of the short fragment was digested without cocaine due to non-specific Exo III digestion (FIGS. 18A and 18B).

Example 11—Exo III-Mediated Target Recycling Using FQ-Modified Short Fragment

A fluorophore-quencher modified version of the short fragment, termed FQ-COC-5325-SF-B, along with COC-5325-LF-P, was used for ultrasensitive cocaine detection via EATR. Specifically, an Iowa Black RQ quencher and a Cy5 fluorophore were modified at the 5' and 3' terminus of the COC-5325-SF-B, respectively. The fluorophore was protected by flanking with an additional thymidine and inverted deoxythymidine at the 3' terminus. Cy5 was chosen as the fluorophore since its emission spectra does not overlap with the spectra emitted by bio-matrices such as saliva.

In the absence of cocaine, the short and long CBSA fragments remain separate and Exo III cannot cleave the abasic site on the short fragment. Because the fluorophore is in close proximity to the quencher, fluorescence is significantly quenched and a minimal fluorescence signal is observed. When cocaine is present, the two CBSA fragments assemble and form a duplexed apurinic site, which is then cleaved by Exo III's apurinic endonuclease activity. Once the short fragment is cleaved, the fluorophore is separated from the quencher, the fluorescence of the solution increases, and the released long fragment and cocaine are recycled for another round of EATR.

Figure 19A:
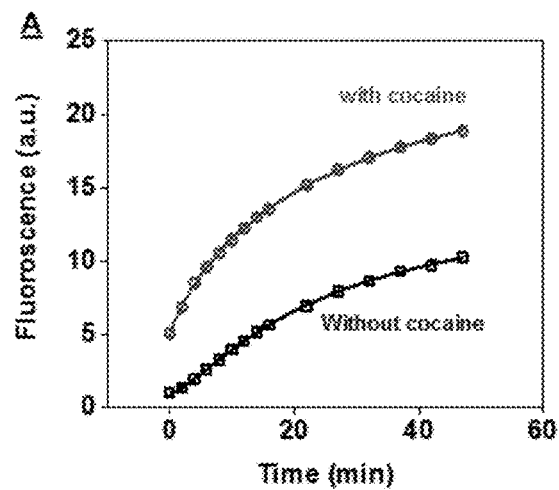
FIGS. 19A-19B show the effect of temperature on CBSA assembly and digestion in a fluorescence assay using 1 μM FQ-COC-5325-SF-B (SEQ ID No: 21) and 1 μM COC-5325-LF-P. Upon the addition of 0.1 U/μL Exo III, relative fluorescence (RF) was recorded over 45 minutes in the absence and presence of 250 μM cocaine at (19A) 23° C. or (19B) 30° C.
Figure 19B:
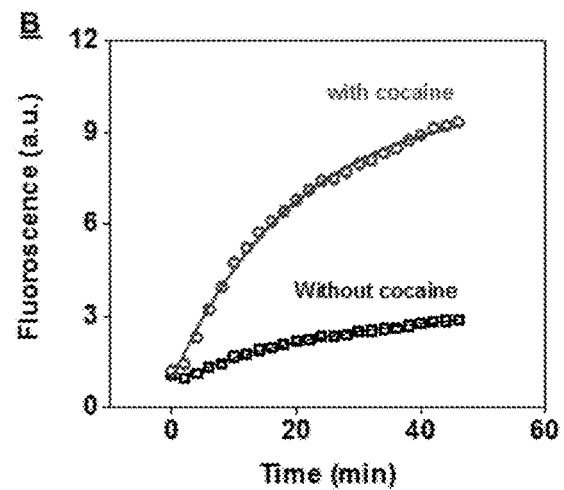

Temperature can greatly affect the hybridization of DNA and may influence the cocaine-induced background assembly of the CBSA. Therefore, the reaction temperature was optimized. Fluorescence increased rapidly at 20° C. upon addition of 0.1 U/μL Exo III without cocaine, implying significant background assembly of the CBSA (FIG. 19A, without cocaine). Upon addition of 50 uM cocaine, the fluorescence intensity increased slightly faster relative to the cocaine-free sample, and a 0.9-fold signal gain was observed after a 45-min digestion (FIG. 19A, with cocaine). At 30° C., the background signal was significantly lower in the absence of cocaine (FIG. 19B, without cocaine). The fluorescence rapidly increased and plateaued after 30 min in the presence cocaine, and a 4-fold signal gain was observed (FIG. 19B, with cocaine). The results indicated that the CBSA fragments cannot assemble spontaneously in the absence of cocaine at 30° C., but assembly can occur when cocaine is present.

Figure 20:
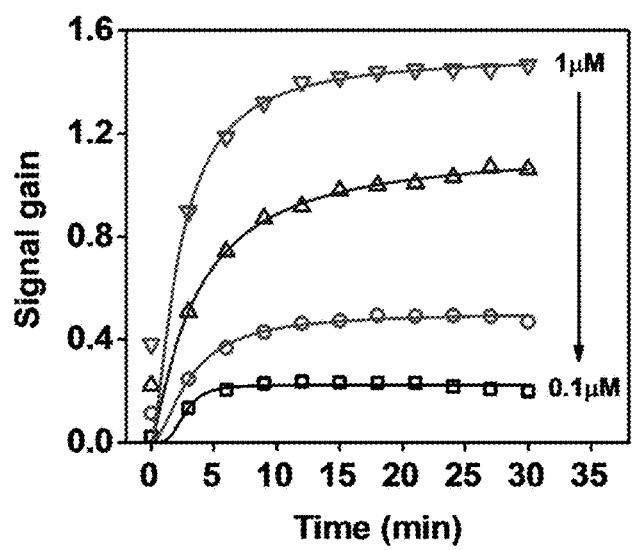
FIG. 20 shows the effect of the concentration of COC-5325-LF-P on CBSA assembly and EATR. 0.1, 0.2, 0.5 and 1 µM of COC-5325-LF-P and 1 µM of FQ-COC-5325-SF-B were used in the EATR assay with 0.1 U/µL Exo III and 50 µM cocaine at 30° C. Signal gain is calculated by $(F-F_0)/F_0 \times 100\%$, where $F_0$ is the fluorescence of this CBSA without cocaine and F is the fluorescence of this CBSA with cocaine.

The concentration of the long fragment also influences the assembly of the CBSA and EATR. This was determined by using 1 μM of FQ-COC-5325-SF-B and varying concentrations of COC-5325-LF-P (0.1 to 1 μM) and digesting the mixtures with Exo III in the presence of 50 μM cocaine. After 30 minutes of digestion, signal gains of 0.2, 0.4, 1.0, and 1.4 were observed for the mixtures containing 0.1, 0.2, 0.5, and 1 μM COC-5325-LF-P, respectively (FIG. 20). The results showed that when higher concentrations of the long fragment were used, the signal gain was higher. This is possibly due to the fact that higher concentrations of the long fragment favor the assembly of CBSA.

Figure 21:
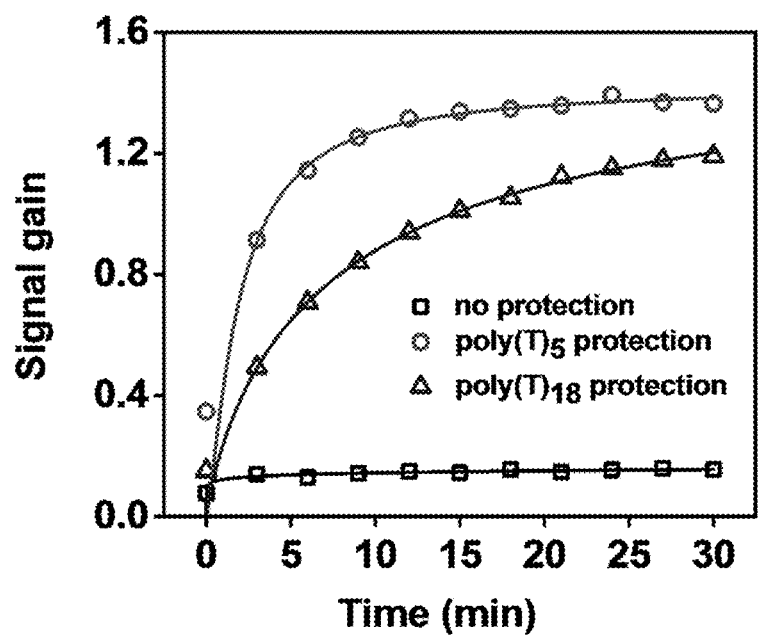
FIG. 21 shows the effect of the length of the poly (T) modification of the long fragment on COC-CBSA-5325 assembly and EATR. 1 µM of FQ-COC-5325-SF-B and 1 µM of COC-5325-LF, COC-5325-LF-P, or COC-5325-LF-P-18 (SEQ ID No: 22) was used in the EATR assay with 0.1 U/µL Exo III and 50 µM cocaine at 30° C. Signal gain is calculated by $(F-F_0)/F_0 \times 100\%$, where $F_0$ is the fluorescence of the CBSAs without cocaine and F is the fluorescence of the CBSAs with cocaine.

Even though the 3' poly $(T)_5$ modification can significantly protect the 3' end of COC-5325-LF-P, the long fragment is still non-specifically and gradually digested during EATR due to the relatively high concentration of enzyme used. To better protect the 3' end of the long fragment, it was modified with a 3' poly $(T)_{18}$ (COC-5325-LF-P-18). 1 μM of COC-5325-LF, COC-5325-LF-P, or COC-5325-LF-P-18 was used with 1 μM FQ-COC-5325-SF-B to perform the EATR experiments with 0.1 U/μL Exo III in the presence and absence of 50 μM of cocaine. The mixture with COC-5325-LF-P showed the highest signal gain within 30 min of enzyme digestion. In contrast, COC-5325-LF was rapidly consumed and was not able to amplify the signal via EATR due to having no 3' protection (FIG. 21). The mixture with COC-5325-LF-P-18 showed slower signal increase compare to COC-5325-LF-P, possibly due to the interference of the long poly $(T)_{18}$ overhang on CBSA assembly and/or Exo III digestion. Therefore, COC-5325-LF-P was chosen for sensor fabrication (FIG. 21).

Figure 22:
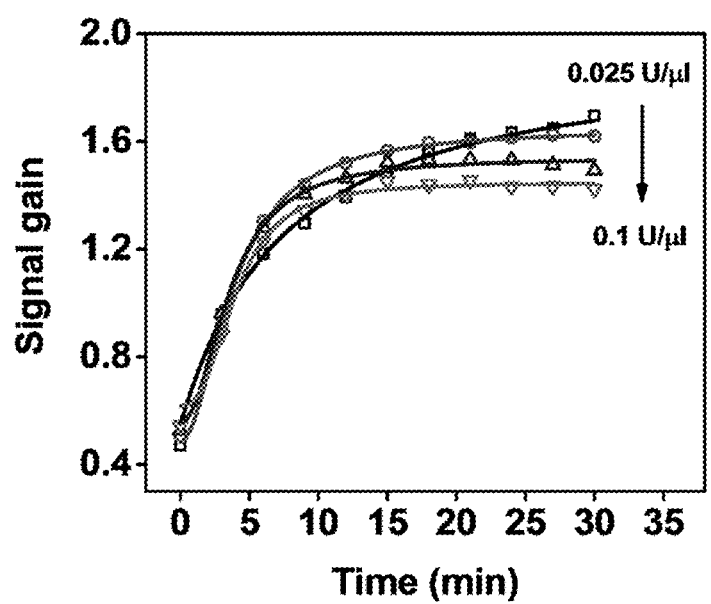
FIG. 22 shows the effect of the Exo III concentration on EATR. 0.025, 0.05, 0.075 and 0.1 U/µL Exo III were used in the EATR assay with 1 µM of COC-5325-LF-P, 1 µM of FQ-COC-5325-SF-B, and 50 µM cocaine at 30° C. Signal gain was calculated by $(F-F_0)/F_0 \times 100\%$, where $F_0$ is the fluorescence of this CBSA without cocaine and F is the fluorescence of this CBSA with cocaine.

Finally, the enzyme concentration was optimized to achieve the shortest reaction time with the largest signal gain. 0.025-0.1 U/μL of Exo III was tested in the fluorescence assay using COC-5325-LF-P and FQ-COC-5325-SF-B as described above. Signal gains of 1.6, 1.6, 1.5, and 1.4 were achieved for enzyme concentrations of 0.025, 0.05, 0.075, and 0.1 U/μL, respectively. Although both the samples containing 0.025 and 0.05 U/μL Exo III showed the highest signal gains, the sample with 0.05 U/μL Exo III had the highest absolute fluorescence increase (FIG. 22), and thus this concentration was used to generate a calibration curve.

Figure 23:
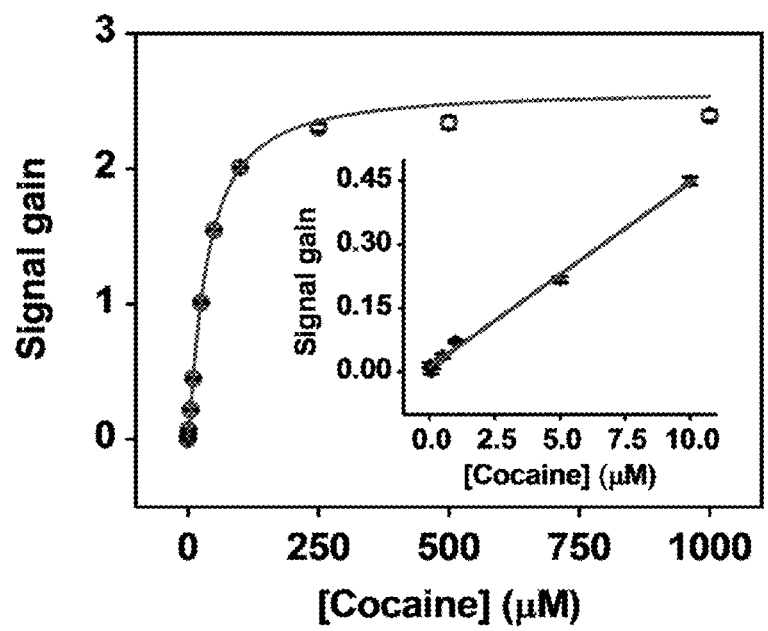
FIG. 23 shows the calibration curve for the CBSA-based EATR cocaine detection assay in buffer. The assay was performed with 1 µM of COC-5325-LF-P, 1 µM of FQ-COC-5325-SF-B, 0.05 U/µL Exo III, and cocaine ranging from 0-1000 µM at 30° C. The signal gain after 30 min of digestion was calculated by $(F-F_0)/F_0 \times 100\%$, where $F_0$ is the fluorescence of this CBSA without cocaine and F is the fluorescence of this CBSA with different concentrations of cocaine. Error bars show the standard deviation of three measurements.

After optimization of all experimental parameters, a calibration curve was generated using different concentrations of cocaine (10 nM-1 mM) (FIG. 23). A linear range was obtained from 0 to 10 μM with a detection limit 100 nM (FIG. 23).

Figure 24:
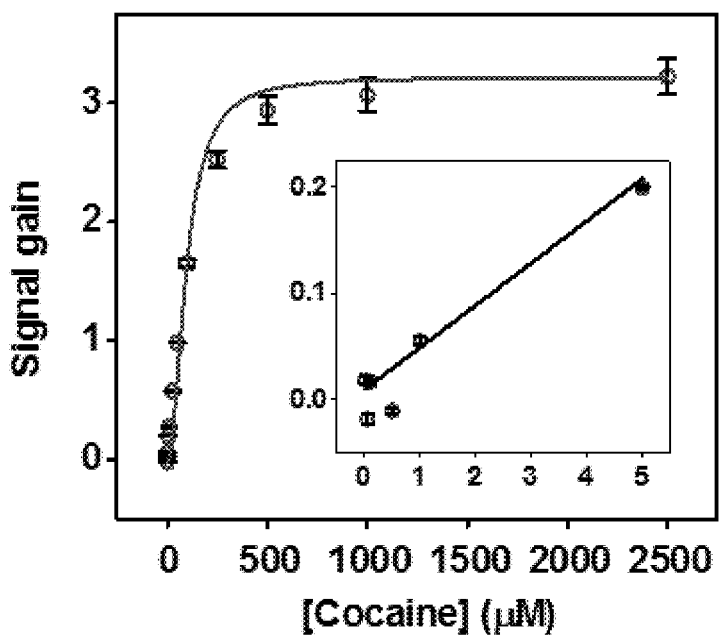
FIG. 24 shows the calibration curve for the CBSA-based EATR cocaine fluorescence detection assay in 20% saliva. The assay was performed with 1 µM of COC-5325-LF-P, 1 µM of FQ-COC-5325-SF-B, 0.05 U/µL Exo III and cocaine ranging from 0-1000 µM at 30° C. The signal gain after 30 min of digestion was calculated by $(F-F_0)/F_0 \times 100\%$, where $F_0$ is the fluorescence of this CBSA without cocaine and F is the fluorescence of this CBSA with different concentrations of cocaine. Error bars show the standard deviation of three measurements.

The CBSA-based EATR assay was then used to detect cocaine in saliva. A calibration curve was established with various concentrations of cocaine (0.1-2500 μM) spiked into 20% saliva (FIG. 24). A linear range was obtained from 0 to 100 μM cocaine with a detection limit of 1 (FIG. 24).

Example 12—Design of the CBSA-Based Colorimetric Assay Employing EATR-Mediated AuNP Aggregation Due to the highly responsive target-induced assembly feature of CBSAs, a similar EATR-amplified strategy can be readily adopted into different sensing platforms using other small-molecule-binding CBSAs. For example, the EATR-amplified assay described above is instrument-dependent, making it unsuitable for instrument-free applications. However, the same strategy can be also used to achieve rapid colorimetric detection of small-molecule targets in an instrument-free fashion.

As a demonstration, the cocaine-binding CBSA, COC-CBSA-5335, was used, which has an $n_H$ of 1.5 and a $K_{1/2}$ of 36 to develop an assay with a visual readout that is potentially suitable for field use. Specifically, the short fragment of this CBSA (SH-COC-5335-SF-1X) was immobilized onto AuNPs, and then the free long fragment (COC-5335-LF) in solution was added (FIG. 25A). In the presence of cocaine, the fragments assemble to form CBSA-cocaine complexes on the particle surface (FIG. 25B). Exo III specifically recognizes the duplexed C3 spacer abasic site between the two binding domains and cleaves the AuNP-conjugated short fragment (FIG. 25C), releasing the intact long fragment and cocaine for another round of target assembly and Exo III cleavage (FIG. 25D). Once all of the short fragments have been cleaved from the particle surface (FIG. 25E), the AuNPs lose their stability under the employed buffer conditions and rapidly aggregate, producing a visible red-to-blue color change (FIG. 25F). The CBSA fragments cannot assemble in the absence of cocaine, precluding Exo III digestion, and the intact short fragments prevent AuNP aggregation such that the solution remains red.

Example 13—EATR of CBSA Mediated by AP Endonuclease of Exo III Instead of its 3'-5' Exonuclease Activity The contribution of Exo III's 3'-5' exonuclease activity to the digestion of CBSA-cocaine complexes relative to its endonucleolytic activity was first investigated by engineering three derivatives of COC-5335-SF. The first derivative (COC-5335-SF-5'A) included a poly $(A)_5$ extension at the 5' end that allows digestion of both the abasic site and the 3' terminus (FIG. 26A). For the second derivative, the poly $(A)_5$ protection was added at the 3' instead of 5' end (COC-5335-SF-3'A), allowing cleavage only at the abasic site (FIG. 26B). For the third derivative (COC-5335-SF-T), the abasic site was replaced with a thymine, allowing digestion only from the 3' terminus (FIG. 26C). A poly $(A)_5$ extension at the 5' end of COC-5335-SF-T was also added to match the length of COC-5335-SF-3'A.

Exo III digestion of a mixture of COC-5335-LF-3'A combined with each of the three different short fragment derivatives was performed in the presence or absence of 250 μM cocaine, and the digestion products were characterized using PAGE. For the COC-5335-SF-5'A, 61% and 5% of the short fragment was cleaved with and without 250 µM cocaine, respectively, after a five-minute enzyme reaction (FIGS. 27A-27C). After 60 minutes, the amount of cleaved COC-5335-SF-5'A increased to 97% and 21%, respectively.

A similar digestion profile for COC-5335-SF-3'A was obtained, where Exo III cleavage occurred only at the abasic site. 61% and 8% of the COC-5335-SF-3'A were respectively cleaved with and without addition of cocaine after five minutes of digestion, which increased to 95% and 17%, respectively, after 60 minutes (FIGS. 28A-28C).

These results demonstrated that the apurinic endonuclease activity of Exo III is efficient enough to mediate the digestion of CBSA-cocaine complexes.

The control experiment with COC-5335-SF-T demonstrated that Exo III was able to remove only one nucleotide from the short fragment. Only 5% of COC-5335-SF-T was digested both with and without cocaine after a five-minute Exo III reaction, and only 15% of the COC-5335-SF-T was digested in the presence of cocaine versus 20% without cocaine after 60 minutes (FIGS. 29A-29C).

It is clear that the CBSA-cocaine complex inhibits the 3'40-5' exonuclease activity of Exo III. Thus, the abasic site is sufficient to enable robust EATR signal amplification, and the poly $(A)_5$ protection at the 3' end of the short fragment is unnecessary.

Figures 30A, 30B:
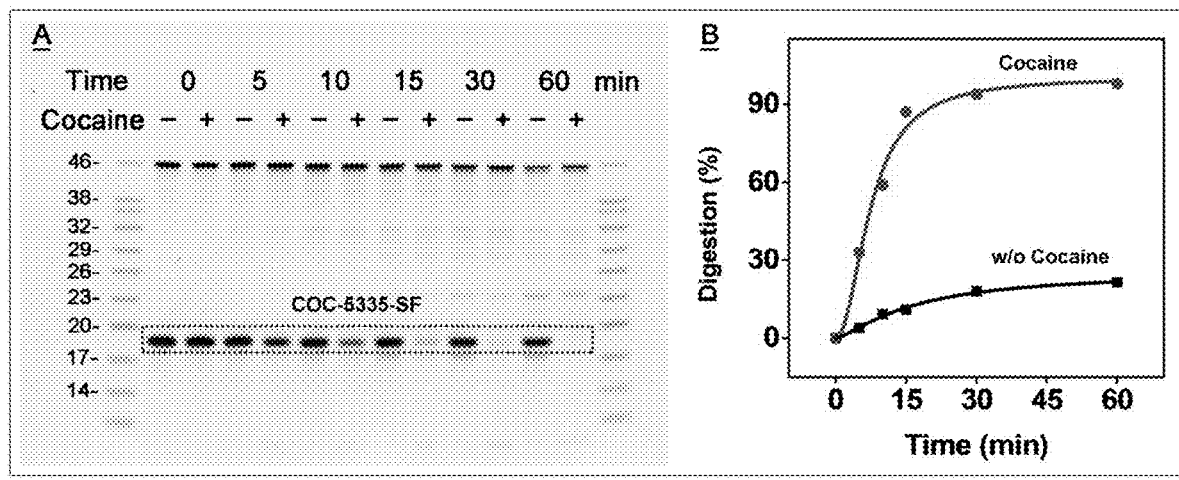
FIGS. 30A-30B show a time-course of Exo III digestion of the cocaine-binding CBSA. (30A) Digestion of a mixture of 1 µM COC-5335-LF-3'A and 8 µM COC-5335-SF by 0.1 U/µL Exo III in the presence or absence of 250 µM cocaine after 5, 10, 15, 30, or 60 minutes of digestion. (30B) Digestion of COC-5335-SF was quantified by $(Int_0-Int)/Int_0 \times 100\%$, where $Int_0$ and Int are the band intensities of either fragment before and after the addition of Exo III, respectively.

To demonstrate EATR with the cocaine-binding CBSA in solution, a time-course of Exo III digestion was performed using COC-5335-LF-3'A and unprotected COC-5335-SF, with a 1:8 ratio of long fragment:short fragment, either with or without 250 µM cocaine. PAGE analysis of the digestion products showed rapid and specific Exo III digestion, with more than 60% of the short fragment cleaved in the presence of cocaine after only 10 minutes (FIGS. 30A-30B). In contrast, less than 5% of the short fragment was cleaved in the absence of cocaine. After a 30-minute reaction, COC-5335-SF was almost completely digested (92%) in the presence of cocaine, while only 14% was digested in the absence of cocaine, demonstrating the specificity of EATR amplification in solution.

Example 14—DNA Surface Coverage and the Length of the Short Fragment Affects EATR-Mediated AuNP Aggregation The CBSA-based EATR-amplified assay was employed to achieve naked-eye detection of cocaine. A thiolated version of COC-5335-SF (Table 1, SH-COC-5335-SF-1X) was conjugated onto AuNPs as described previously.[13] Because DNA surface coverage has a critical influence on EATR-mediated AuNP aggregation, a simple strategy was developed for generating AuNPs displaying different quantities of short fragment. This was done by incubating short fragment-saturated AuNPs with various micromolar concentrations of DTT to displace different quantities of immobilized short fragment from the particle surface. Then, the surface coverage resulting from treatment with various DTT concentrations was measured by mixing each of these batches of AuNPs with an equal volume of 1.0 M DTT and incubating overnight to remove all remaining DNA strands from the particle surface. These were subsequently quantified by centrifuging the samples and measuring the DNA concentration in the collected supernatant with OliGreen, a DNA binding dye.

Figures 31A, 31B:
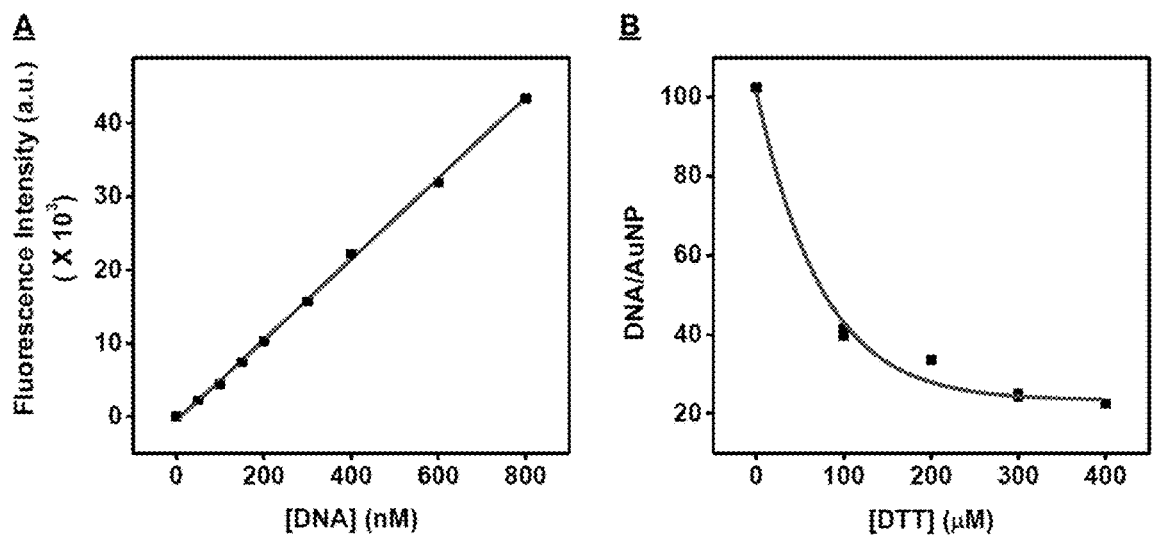
FIG. 31A-31B show the characterization of surface coverage of SH-COC-5335-SF-1X-modified AuNPs treated with different concentrations of DTT. (31A) A standard calibration curve established with known concentrations of SH-COC-5335-SF-1X was used to calculate the DNA surface coverage of the DTT-treated AuNPs. (31B) Surface coverage decreased with increasing amounts of DTT employed during the treatment procedure. Error bars show standard deviations obtained from three measurements.

A calibration curve (FIG. 31A) determined that treatment with DTT concentrations of 0, 100, 200, 300, and 400 µM produced AuNPs that respectively displayed 102±1, 41±1, 34±1, 25±1, and 22±1 strands/particle (FIG. 31B).

This demonstrates that DTT treatment can effectively regulate DNA surface coverage on AuNPs in a concentration-dependent manner. AuNPs treated with 500 µM DTT yielded a surface coverage of 20±1 strands/particle; the resulting particles were unstable, and spontaneously aggregated in the reaction buffer. Thus, these AuNPs were omitted from following experiments.

How differing levels of surface coverage affect CBSA-cocaine assembly, exonuclease cleavage, and AuNP aggregation was then assessed. Because the CBSA will be assembled on the particle, Exo III will have minimal accessibility to the 3' end of the long fragment. Various batches of 5 nM SH-COC-5335-SF-1X-modified AuNPs with 100 nM COC-5335-LF were incubated in the presence or absence of 250 µM cocaine for 30 minutes, and then 0.2 U/µL Exo III was added. The signal response was tracked by performing time-dependent measurements of UV-vis absorbance. Well-dispersed AuNPs have an absorbance peak at 520 nm; as AuNPs start to aggregate, this peak decreases and a new peak appears at 650 nm. Therefore, the ratio of $A_{650}/A_{520}$ was used to evaluate EATR-mediated AuNP aggregation. When the value of $A_{650}/A_{520}$ is below 0.4, the AuNPs are well separated and the solution appears red. When the value of $A_{650}/A_{520}$ is 0.6, the AuNPs begin to aggregate and the solution appears purple. A value of $A_{650}/A_{520}>0.8$ indicates complete aggregation, and the solution appears dark blue. SH-COC-5335-SF-1X-modified AuNPs with relatively low surface coverage (25 strands/particle) demonstrated much faster aggregation than AuNPs with high surface coverage (102 strands/particle) (FIGS. 32A-32F). No aggregation was observed for these 102 strands/particle AuNPs, even 70 minutes after the addition of Exo III (FIG. 32A). Likewise, no visible color change was observed at a surface density of 41 strands/particle (FIG. 32B). However, further reductions in surface coverage produced a clear increase in the rate of AuNP aggregation, and AuNPs with surface coverages of 34, 25 and 22 strands/particle produced a dark blue color ($A_{650}/A_{520} \geq 0.8$) within 72, 52, and 38 minutes of Exo III digestion, respectively. This indicates both specific CBSA-cocaine assembly and successful EATR amplification. In the meantime, the AuNPs remained well-dispersed at all levels of surface coverage and all target-free samples remained red ($A_{650}/A_{520}=0.4$) (FIGS. 32C-32E). Notably, both target- and non-target-mediated Exo III digestion and AuNP aggregation are more pronounced for AuNPs with lower surface coverages. 25 strands/particle were identified as the optimal level of surface coverage for the assay due to the existence of detection window during which the drug-containing sample is blue while the drug-free sample remains red (FIG. 32F).

Although the ratio between COC-5335-LF and AuNP-conjugated SH-COC-5335-SF-1X under this optimal surface coverage was close to 1:1, Exo III-mediated recycling of the long fragment and target was taking place on the particle surface since DNA hybridization efficiency on AuNPs is usually below 20%. The DTT-based strategy for regulating DNA surface coverage plays multiple roles in facilitating exonuclease digestion of AuNP-conjugated short fragments for rapid cocaine detection. First, it prevents non-specific binding of DNA bases by occupying vacant areas on the particle surface with DTT, lifting the covalently-bound aptamer fragments into an upright orientation that increases CBSA-target assembly and enzyme accessibility. Second, it adjusts the surface density by replacing some of the chemically-bound aptamer fragments. This significantly reduces the steric and electrostatic repulsion caused by neighboring DNA strands, enabling optimized CBSA-cocaine complex assembly. Finally, by decreasing DNA surface coverage, this treatment also decreases local salt concentration at the surface, which greatly reduces the salt-induced inhibition of Exo III.

A longer version of SH-COC-5335-SF-1X should further increase the stability of the modified AuNPs by suppressing nonspecific digestion-mediated aggregation. Thus, a new construct (Table 1, SH-COC-5335-SF-2X) comprising two tandem abasic-site-incorporated short fragment repeats with a $(T)_6$ linker was designed, hereon termed SH-COC-5335-SF-2X. The assay's specificity should be enhanced by this change, because Exo III will have to cleave both abasic sites in order to trigger cocaine recycling and AuNP aggregation (FIGS. 33A-33F).

Then, 13-nm AuNPs modified with SH-COC-5335-SF-2X were synthesized and the DTT regulation strategy was used to adjust the surface coverage of the AuNPs. The effects of DNA surface coverage on EATR performance was tested. A calibration curve (FIG. 34A) determined that treatment with DTT concentrations of 0, 200, 300, 400, and 500 μM produced AuNPs that respectively displayed 83±2, 23±1, 20±1, 18±1, and 16±1 strands per particle (FIG. 34B). As expected, increasing concentrations of DTT produced AuNPs with lower levels of surface coverage (FIGS. 34A-34B).

Compared to SH-COC-5335-SF-1X modified-AuNPs, SH-COC-5335-SF-2X modified-AuNPs are stable even with surface coverages as low as 16 strands/particle. This is most likely due to the increased number of negatively charged DNA-phosphate groups located on the AuNP surface, providing more repulsion among particles. Lower-coverage AuNPs underwent EATR-mediated AuNP aggregation at a much faster rate than those with saturating surface coverage (FIGS. 35A-35E). The surface coverage of 20±1 strands/particle was selected due to a combination of short reaction time and long detection window (FIG. 35F).

Example 15—Visual Detection of Cocaine Using CBSA-Based EATR-Amplified Colorimetric Assay The assay's performance with SH-COC-5335-SF-1X was compared versus SH-COC-5335-SF-2X at optimized surface coverage. SH-COC-5335-SF-2X-modified AuNPs aggregated more rapidly than those modified with SH-COC-5335-SF-1X (FIG. 36). Then, SH-COC-5335-SF-2X-modified AuNPs were used to test the sensitivity of the assay. The particles remained stable in the reaction buffer, and the color of the sample was not affected by cocaine concentrations of up to 500 μM in the absence of Exo III (FIG. 37A, 0 min). Upon addition of Exo III, samples containing cocaine demonstrated different levels of particle aggregration, resulting in a distinctive color readout that shifted from light purple, dark purple, to dark blue at increasing drug concentrations over the course of 20 minutes (FIG. 37A, 20 min), with $A_{650}/A_{520}$ varying from 0.39 (0.2-1 μM) to 0.90 (500 μM). The color of the cocaine-free sample remained unchanged. A clear blue color in samples containing as little as 10 μM cocaine was observed with the naked eye after 20 minutes (FIG. 37A). Using UV-vis spectroscopy measurements, a measurable limit of detection of 2 μM (FIG. 37B) was obtained.

The target-specificity of the CBSA-based EATR-amplified colorimetric assay was determined by challenging it with cocaine along with common cutting agents observed in street samples such as lidocaine, caffeine, levamisole, and benzocaine at a concentration of 50 μM. A red-to-blue color change was observed only in the cocaine-containing sample within 20 minutes (FIG. 38). These results show that the EATR colormietric assay can be used for the specific and sensitive naked-eye detection of cocaine in seized samples.

This assay facilitated rapid, naked-eye detection of cocaine at low micromolar concentrations and is more sensitive, robust, or simple compared to previously reported methods for the visual detection of cocaine (Table 2).

TABLE 2

Comparison of assays for the visual detection of cocaine.

| Detection strategy | Visual Detection Limit | Detection Time | Existing Problems | Reference |
| --- | --- | --- | --- | --- |
| CBSA-based EATR-amplified assay | 10 μM | 20 min | Requires enzyme reaction | This work |
| Dissociation of aptamer-hybridized DNA-conjugated AuNP-assemblies | 500 μM | 1 min | Preparation of AuNP assemblies is laborious | Liu et al. *Angew. Chem., Int. Ed.* 2006, 45, 90-94. |
| Dye-displacement assay | 500 μM | Overnight | Long reaction time | Stojanovic et al. *J. Am. Chem. Soc.* 2002, 124, 9678-9679. |
| Aggregation of split aptamer-protected unmodified AuNPs | 50 μM | 3 min | Unmodified AuNPs are unstable | Zhang et al. *Small* 2008, 4, 1196-1200. |
| AuNP and conjugated polyelectrolyte | 50 μM | 2 min | Unmodified AuNPs are unstable | Xia et al. *Proc. Natl. Acad. Sci. U.S.A.* 2010, 107, 10837-10841. |
| Target-induced dissociation of aptamer-linked hydrogels | 2 μM | 10 min | Enzyme-embedded hydrogel is hard to preserve | Zhu et al. *Angew. Chem., Int. Ed.* 2010, 49, 1052-1056. |

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The description herein of any aspect or embodiment of the invention using temis such as "comprising," "having," "including" or "containing" with reference to an element or elements is intended to provide support for a similar aspect or embodiment of the invention that "consists of," "consists essentially of," or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A cooperative binding split aptamer (CBSA)-based enzyme-assisted target recycling (EATR)-amplified sensor comprising a CBSA, wherein the CBSA comprises SEQ ID NO:8 and SEQ ID NO:2.

2. The CBSA-based EATR-amplified sensor according to claim 1, the CBSA being modified by addition of a reporter label.

3. The CBSA-based EATR-amplified sensor according to claim 2, the reporter label being a fluorescent dye, a gold nanoparticle (AuNP), or a fluorescent dye and quencher pair.

4. A cooperative binding split aptamer (CBSA)-based enzyme-assisted target recycling (EATR)-amplified sensor comprising a CBSA, wherein the CBSA comprises SEQ ID NO:3 and SEQ ID NO:2.

5. A method for detecting dehydroisoandrosterone-3-sulfate (DIS) in a sample comprising contacting the sample with the CBSA-based EATR-amplified sensor of claim 4.

6. The method according to claim 5, the CBSA being recognized and cleaved by Exo III at a C3 spacer abasic site.

7. The method according to claim 5, the sample being selected from blood, plasma, urine, tears, and saliva.

8. The method according to claim 5, the method further comprising detecting a signal, the signal being a change in fluorescence intensity.

* * * * *